US008574872B2

(12) United States Patent
Minato et al.

(10) Patent No.: US 8,574,872 B2
(45) Date of Patent: Nov. 5, 2013

(54) MULTIMER OF EXTRACELLULAR DOMAIN OF CELL SURFACE FUNCTIONAL MOLECULE

(75) Inventors: Nagahiro Minato, Kyoto (JP); Yoshimasa Tanaka, Kyoto (JP); Shiro Shibayama, Ibaraki (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 13/486,189

(22) Filed: Jun. 1, 2012

(65) Prior Publication Data

US 2012/0269859 A1    Oct. 25, 2012

Related U.S. Application Data

(63) Continuation of application No. 12/281,427, filed as application No. PCT/JP2007/054052 on Mar. 2, 2007, now Pat. No. 8,216,996.

(30) Foreign Application Priority Data

Mar. 3, 2006   (JP) ................................ 2006-057373

(51) Int. Cl.
 *C12P 21/04*   (2006.01)
 *C07K 14/00*   (2006.01)

(52) U.S. Cl.
 USPC ......................................... 435/69.7; 530/350

(58) Field of Classification Search
 None
 See application file for complete search history.

(56) References Cited

U.S. PATENT DOCUMENTS

| 2003/0232323 | A1 | 12/2003 | Freeman et al. |
| 2004/0157296 | A1 | 8/2004 | Yang et al. |

FOREIGN PATENT DOCUMENTS

| WO | 95/01994 | A1 | 1/1995 |
| WO | 01/83750 | A2 | 11/2001 |
| WO | 01/83750 | A3 | 11/2001 |
| WO | 02/078731 | A1 | 10/2002 |
| WO | 02/086083 | A2 | 10/2002 |
| WO | 02079474 | A2 | 10/2002 |
| WO | 03/010202 | A1 | 2/2003 |
| WO | 03/042402 | A2 | 5/2003 |
| WO | 2004/076479 | A2 | 9/2004 |
| WO | 2007124283 | A2 | 11/2007 |

OTHER PUBLICATIONS

Freeman et al., "Engagement of the PD-1 Immunoinhibitory Receptor by a Novel B7 Family Member Leads to Negative Regulation of Lymphocyte Activation", J. Exp. Med., vol. 192, No. 7, Oct. 2, 2000, pp. 1027-1034.*
European Patent Office, Extended European Search Report issued May 8, 2009 in corresponding EP Application No. 07715146.2 (in the name of Kyoto University et al.).
European Patent Office, European Office Action issued Feb. 5, 2010 in corresponding EP Application No. 07715146.2 (in the name of Kyoto University et al.).
European Patent Office, European Office Action issued Oct. 11, 2011 in corresponding EP Application No. 07715146.2 (in the name of ONO Pharmaceutical Co., Ltd.).
Yasumasa Ishida et al., "Induced expression of PD-1, a novel member of the immunoglobulin gene superfamily, upon programmed cell death," The EMBO Journal, 1992, 11(11): 3887-3895.
Yoshiko Iwai et al., "Involvement of PD-L1 on tumor cells in the escape from host immune system and tumor immunotherapy by PD-L1 blockade", PNAS, 2002, 99(19): 12293-12297.
John R. Sedy et al., "B and T lymphocyte attenautor regulates T cell activation through interaction with herpesvirus entry mediator", Nature Immunology, 2005, 6(1): 90-98.
Seigo Terawaki et al., Dai 34 Kai the Japanese Society for Immunology Gakujutsu Shukkai Kiroku, 2-G-W30-31-P, 2004, p. 224.
Thomas A. Waldmann, "Effective Cancer Therapy Through Immunomodulation", Annual Review of Medicine, 2006, 57: 65-81.
Xuewu Zhang et al., "Structural and Functional Analysis of the Costimulatory Receptor Programmed Death-1", Immunity, 2004, 20: 337-347.
European Patent Office, European Search Report dated May 25, 2012 in corresponding Application No. 12153114.
Blank et al., Cancer Immunology, Immunotherapy, Springer, 2005, 54, 4, 307-314.
European Patent Office, Office Action dated Jan. 30, 2013, issued in counterpart European Patent Application No. 12 153 114.9.

* cited by examiner

*Primary Examiner* — Suzanne M Noakes
(74) *Attorney, Agent, or Firm* — Sughrue Mion, PLLC

(57) ABSTRACT

As a substance which pharmacologically regulates the function of a cell surface functional molecule, a substance which has specificity and an activity or efficacy equal or superior to an antibody and does not require an advanced production technique and facility for application thereof to a pharmaceutical product has been demanded. The invention relates to a multimer of an extracellular domain of a cell surface functional molecule, particularly a tetramer of an extracellular domain of PD-1 or PD-L1. Further, the invention relates to an application of such a tetramer as a preventive and/or therapeutic agent for cancer, cancer metastasis, immunodeficiency, an infectious disease or the like and an application of PD-1 or PD-L1 as a testing or diagnostic agent or a research agent for such a disease.

13 Claims, 5 Drawing Sheets

US 8,574,872 B2

MULTIMER OF EXTRACELLULAR DOMAIN OF CELL SURFACE FUNCTIONAL MOLECULE

CROSS REFERENCE TO RELATED APPLICATIONS

This is a continuation of U.S. patent application Ser. No. 12/281,427, filed Sep. 2, 2008 (U.S. Pat. No. 8,216,996), which is a 371 National Stage Entry of PCT/JP2007/054052, filed Mar. 2, 2007, the disclosures of which are incorporated herein in their entirety.

TECHNICAL FIELD

The present invention relates to a polypeptide, wherein the extracellular domains of the cell surface functional molecule are multimerized, a derivative thereof, a pharmaceutical composition containing it as an active ingredient, a polynucleotide encoding the polypeptide, a transformant by the polynucleotide, and methods for producing them, and uses thereof.

BACKGROUND ART

Programmed Cell Death 1, or PD-1 (also referred to as PDCD1) related to the present invention is a 50 to 55 kD type I membrane glycoprotein (see Non-Patent Document 1). The expression is recognized in thymocytes when $CD4^-CD8^-$ cells are differentiated, while it is recognized in an activated $CD4^-CD8^-$ cells, T-cells, B-cells and monocytes in the peripheral.

PD-1 has an ITIM motif and an ITSM motif in the intracellular domain, which function as inhibitory domains. It is considered that phosphatases, i.e., SHP-1 and SHP-2, mutually interact in the domain to take charge of a suppression function against T-cell receptor complexes.

It has been reported that PD-1 gene is one of genes responsible for autoimmune diseases, such as systemic lupus erythematodes (see Non-Patent Document 2). It has also been indicated that PD-1 serves as a regulatory factor for onset of autoimmune diseases, particularly for peripheral self tolerance, on the ground that PD-1-deficient mice develop lupus autoimmune diseases, such as glomerulonephritis and arthritis (see Non-Patent Documents 3 and Non-Patent Document 4), and dilated cardiomyophathy-like disease (see Non-Patent Document 5).

There are two substances that have been identified as ligands of PD-1: Programmed Death Ligand 1, or PD-L1 (also known as PDCD1L1 or B7-H1) (see Non-Patent Document 6), and Programmed Death Ligand 2, or PD-L2 (also referred to as PDCD1L2 or B7-DC) (see Non-Patent Document 7).

Expression of PD-L1 has been verified not only in immune cells, but also in certain kinds of tumor cell lines (such as monocytic leukemia-derived cell lines, mast cell tumor-derived cell lines, hepatoma-derived cell lines, neuroblastoma-derived cell lines, and various mammary tumor-derived cell lines) and in cancer cells derived from diverse human cancer tissues (see Non-Patent Document 7). Likewise, expression of PD-L2 has been verified in Hodgkin's lymphoma cell lines and others. There is a hypothesis that some of the cancer or tumor cells take advantage from interaction between PD-1 and PD-L1 or PD-L2, for suppressing or intercepting T-cell immune responses to their own (see Non-Patent Document 8).

There are some reports regarding substances inhibiting immunosuppressive activity of PD-1, or interaction between PD-1 and PD-L1 or PD-L2, as well as the uses thereof. A PD-1 inhibitory antibody or a PD-1 inhibitory peptide is reported in Patent Document 1, Patent Document 2, and Patent Document 3. On the other hand, a PD-L1 inhibitory antibody or a PD-L1 inhibitory peptide is reported in Patent Document 4, Patent Document 5, Patent Document 6, and Patent Document 7. A PD-L2 inhibitory antibody or a PD-L2 inhibitory peptide is reported in Patent Document 5 and Patent Document 8.

However, there has been no report regarding a multimer of the present invention, which is formed in the extracellular domains of PD-1, PD-L1 or PD-L2. Further, it has not yet been reported that the multimer is able to be used as a labeling agent of high specificity for detection of cell surface functional molecules such as PD-1.

Patent Document 1: JP 2003-507491
Patent Document 2: WO 2004/004771
Patent Document 3: WO 2004/056875
Patent Document 4: JP No. 2004-533226
Patent Document 5: JP 2005-509421
Patent Document 6: WO 2002/086083
Patent Document 7: WO 2001/039722
Patent Document 8: JP 2004-501631
Non-Patent Document 1: Shinohara T et al, *Genomics*, 1994, Vol. 23, No. 3, pp. 704-706
Non-Patent Document 2: Prokunina L et al, *Nature Genetics*, 2002, Vol. 32, No. 4, pp. 666-669
Non-Patent Document 3: Nishimura H et al, *International Immunology*, 1998, Vol. 10, No. 10, pp. 1563-1572
Non-Patent Document 4: Nishimura H at al, *Immunity*, 1999, Vol. 11, No. 2, pp. 141-151
Non-Patent Document 5: Nishimura H at al, *Science*, 2001, Vol. 291, No. 5502, pp-319-332
Non-Patent Document 6: Freeman G J et al, *Journal of Experimental Medicine*, 2000, Vol. 19, No. 7, pp. 1027-1034
Non-Patent Document 7: Latchman Y at al, *Nature Immunology*, 2001, Vol. 2, No. 3, pp. 261-267
Non-Patent Document 8: Iwai Y et al, *Proceedings of the National Academy of Science of the United States of America*, 2002, Vol. 99, No. 19, pp. 12293-12297

DISCLOSURE OF THE INVENTION

Problems to be Solved by the Invention

A substance that pharmacologically controls the function of a cell surface functional molecule includes an antibody against the cell surface functional molecule, or a decoy as a modified ligand of the cell surface functional molecule.

Usually, when an antibody is formulated into medical supplies, the antibody is humanized or modified into a human-type antibody in order to evade the antigenicity. However, it requires highly advanced technology and facilities for the humanized or human-type antibody to be developed or produced. On the other hand, when the decoy is formulated into medical supplies, the process does not require technology and facilities as highly advanced as the antibody drug does. However, the low activity and efficacy hinders the development.

It is required to develop a substance that solves these problems, that is, a substance that has specificity, activity and efficacy on the same level as or superior to those of the antibody, and that does not require advanced production technology and facilities for formulation into medical supplies.

Means for Solving the Problems

The present inventors had intensively studied so as to solve the above problems and found that the multimer of the extracellular domains of the cell surface functional molecule solves the problems above. Thus, they have completed the invention as one of the examples, regarding the multimer of the extracellular domains of PD-1 or the ligand, PD-L1 or PD-L2.

Furthermore, the present inventors had verified that the multimer had immunopotentiating effect. This led to the discovery that the multimer could serve as a preventive and/or therapeutic drug for cancers, cancer metastasis, immune deficiency syndrome and infectious diseases. On the other hand, the present inventors had paid attention to the fact that the antibody was bound to an Fc receptor on the surface of an immune cell, and formed a non-specific binding in some cases. They verified that the multimer of the extracellular domains was specifically bound to the cell surface functional molecule, or a ligand of the multimer, and found that the labeling agent thereof is useful as a test agent or diagnostic drug for the above diseases, as well as a research reagent for the cell surface functional molecule.

The present invention includes the following elements:
(1) a multimer comprising 2 to 10 extracellular domains of PD-1;
(2) the multimer according to the above (1), wherein the extracellular domains of PD-1 are serially-concatenated directly or with peptide linkers;
(3) the multimer according to the above (1), wherein the extracellular domains of PD-1 are those in which 1 to 3 amino acids in 25th to 145th domains of human or mouse PD-1 are substituted with other amino acids;
(4) the multimer according to the above (1), wherein the number of the extracellular domains is 4;
(5) the multimer according to the above (2), wherein the extracellular domains of PD-1 are serially-concatenated with peptide linkers;
(6) the multimer according to the above (5), wherein each peptide linker comprises 2 to 15 amino acids;
(7) the multimer according to the above (6), comprising the amino acid sequence of SEQ ID NO 1 or 3;
(8) a polynucleotide encoding the multimer described in the above (1);
(9) the polynucleotide according to the above (8), encoding the multimer described in the above (7);
(10) the polynucleotide according to the above (9), comprising the nucleotide sequence of SEQ ID NO: 2 or 4;
(11) an expression vector in which the polynucleotide described in the above (8) is incorporated;
(12) a transformant transformed by the expression vector described in the above (11);
(13) a multimer comprising 2 to 10 extracellular domains of PD-L1;
(14) the multimer according to the above (13), wherein the extracellular domains of PD-L1 are serially-concatenated directly or through linkers;
(15) the multimer according to the above (13), wherein the extracellular domains of PD-L1 are those in which 1 to 3 amino acids in 18th to 230th domains of human PD-L1, or 18th to 229th domains of mouse PD-L1 are substituted by other amino acids;
(16) the multimer according to the above (13), wherein the number of the extracellular domains is 4;
(17) the multimer according to the above (14), wherein the extracellular domains of PD-L1 are serially-concatenated with peptide linkers;
(18) the multimer according to the above (17), wherein each peptide linker comprises 2 to 15 amino acids;
(19) the multimer according to the above (18), comprising the amino acid sequence of SEQ ID NO: 5 or 7;
(20) a polynucleotide encoding the multimer described in the above (13);
(21) the polynucleotide according to the above (20), encoding the multimer described in the above (19);
(22) the polynucleotide according to the above (21), comprising the nucleotide sequence of SEQ ID NO: 6 or 8;
(23) an expression vector in which the polynucleotide described in the above (22) is incorporated;
(24) a transformant transformed by the expression vector described in the above (23);
(25) a method for producing the multimer described in the above (1) or (13), comprising the steps of (i) culturing the transformant described in the above (12) or (24), (ii) destroying the transformant by ultrasonic waves, lysozyme treatment and/or freeze-thaw, and (iii) purifying by salting-out, solvent precipitation, dialysis, ultrafiltration, gel filtration or SDS-polyacrylamide gel electrophoresis, ion exchange chromatography, affinity chromatography, hydrophobic chromatography, reverse phase chromatography and/or isoelectric focusing electrophoresis;
(26) a pharmaceutical composition comprising the multimer described in the above (1) or (13) as an active ingredient;
(27) the pharmaceutical composition according to the above (26), which is a preventive and/or therapeutic agent for cancers, cancer matastasis, immune deficiency syndrome or infectious diseases;
(28) an agent comprising the multimer described in the above (1) or (13) and one or more selected from chemotherapy drugs, cancer treatment adjuvants, immunomodulators, cancer antigens, antiviral agents, antibiotic preparations, antimicrobials, fungal treatments and vaccines;
(29) a method for prevention and/or treatment of diseases selected from cancers, cancer matastasis, immune deficiency syndrome and infectious diseases, comprising administering an effective dose of the multimer comprising 2 to 10 extracellular domains of PD-1 to mammals;
(30) use of the multimer comprising 2 to 10 extracellular domains of PD-1 for production of a preventive and/or therapeutic agent for diseases selected from cancers, cancer matastasis, immune deficiency syndrome and infectious diseases;
(31) a method for prevention and/or treatment of diseases selected from cancers, cancer matastasis, immune deficiency syndrome and infectious diseases, comprising administering an effective dose of the multimer comprising 2 to 10 extracellular domains of PD-L1 to mammals;
(32) use of the multimer containing 2 to 10 extracellular domains of PD-L1 for production of a preventive and/or therapeutic agent for diseases selected from cancers, cancer matastasis, immune deficiency syndrome and infectious diseases;
(33) a PD-L1 detection reagent comprising the multimer comprising 2 to 10 extracellular domains of PD-1; and
(34) a PD-1 detection reagent comprising the multimer comprising 2 to 10 extracellular domains of PD-L1.

Effect of The present Invention

The multimer comprising the extracellular domains of PD-1 or PD-L1 related to the present invention possesses high antagonistic activity to its ligand, PD-L1 or PD-1, respectively. It also stimulates the proliferation of lymphoid cells and enhances their cellular cytotoxicities.

Further, the labeling agent of the multimer never exhibits a non-specific binding that is more or less observed in antibodies. Thus, the labeling agent is excellent as a detection reagent that permits detection of each ligand in a highly specific manner.

BEST MODE FOR CARRYING OUT THE INVENTION

Multimer

In the present invention, the "multimer" means a polypeptide comprising 2 to 10 extracellular domains of the cell surface functional molecule or the salts thereof, and hereinafter, it may be abbreviated to "the multimer of the present invention". Herein, "the extracellular domains of the cell surface functional molecule" that constitute the multimer include the extracellular domain separated from a wild-type cell surface functional molecule, and the entire or partial region of a free cell surface functional molecule, etc. Further, they also include those with the identical functions as the extracellular domains or free cell surface functional molecule, despite that some of amino acids in the amino acid sequence (preferably one to three, and more preferably one amino acid) are modified by means of deletion, substitution or insertion with other amino acids, or combination thereof (hereinafter, sometimes abbreviated to "the extracellular domains or the like"). Although the positions where the amino acids are deleted, substituted or inserted, as well as the kind of amino acid to be substituted are not particularly limited, it is preferred that the modification be performed for enhancing the refolding or binding activity.

In the present invention, the description that the extracellular domains of the cell surface functional molecule "are serially-concatenated directly" means that the C-terminal of the extracellular domain is directly bound to the N-terminal of another extracellular domain.

In the present invention, the description that the extracellular domains of the cell surface functional molecule "are serially-concatenated through peptide linkers" means that the C-terminal of the extracellular domain is bound to the N-terminal of another extracellular domain through a peptide linker. In the present invention, "peptide linker" is a polypeptide comprising 2 to 15 amino acids, and may be encoded as a part of the polynucleotide encoding the multimer of the present invention.

The multimer of the present invention also includes that in which the extracellular domains of the cell surface functional molecule are bound through non-peptide linkers. Herein, "the extracellular domains of the cell surface functional molecule are bound through non-peptide linkers" means that any of the terminals are mutually bound through non-peptide linkers, and that each extracellular domain or the like is bound to a proper carrier.

The C-terminal of the multimer of the present invention may be any of a carboxyl group, an amide group or an ester group. When the multimer of the present invention has a carboxyl group at other than the C-terminal, the carboxyl group may be amidated or esterified.

The multimer of the present invention may be that in which an amino group of an amino acid residue (e.g., methionine residue) at the N-terminal is protected with a protecting group (e.g., C1-C6 acyl groups including a formyl group and an acetyl group), that in which a glutamine residue at the N-terminal produced by intravital digesting is pyroglutaminated, that in which a substituent (e.g., —OH, —SH, an amino group, an imidazole group, an indole group and a guanidino group) on the side chain of an amino acid within the molecule is protected with a proper protecting group (e.g., C1-C6 acyl groups including a formyl group and an acetyl group), or that in which sugar chains are bound.

It is preferred that the salts of the multimer of the present invention be those pharmaceutically acceptable ones. Examples of the salts include alkali metal (e.g., potassium and sodium) salts, alkaline earth metal (e.g., calcium and magnesium) salts, an ammonium salt, pharmaceutically acceptable organic amine (e.g., tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine and N-methyl-D-glucamine) salts, and acid addition salts (e.g., inorganic acid salts such as hydrochloride, hydrobromide, hydroiodide, sulfate, phosphate and nitrate, and organic acid salts such as acetate, lactate, tartrate, benzoate, citrate, methanesulfonate, ethanesulfonate, benzenesulfonate, toluenesulfonate, isethionate, glucuronate and gluconate). Further, it is preferred that the salts of the multimer of the present invention be water-soluble.

The salts of the multimer of the present invention can be converted into solvates. It is preferred that the solvates be non-toxic and water-soluble. Examples of the proper solvates include solvates with solvents such as water or an alcohol-based solvent (e.g., ethanol).

Examples of PD-1, the cell surface functional molecule of the present invention, include human PD-1 (hereinafter sometimes abbreviated to hPD-1) and the corresponding immunoreceptors of mammalian. Herein, the mammals include a chimpanzee, cynomolgus monkey, mouse, rat, guinea pig, dog and pig. Particularly, the human PD-1 is constituted by the amino acid sequence that is identified by GenBank Accession. No. NP_005009 or NP_005009.1, while the mouse PD-1 (hereinafter sometimes abbreviated to mPD-1) is constituted by the amino acid sequence that is identified by GenBank Accession. No. NP_032824 or NP_032824.1.

Examples of PD-L1 include human PD-L1 (hereinafter sometimes abbreviated to hPD-L 1) and the corresponding immunoreceptors of mammalian. Herein, the mammals include a chimpanzee, cynomolgus monkey, mouse, rat, guinea pig, dog and pig. Particularly, the human PD-L1 is constituted by the amino acid sequence that is identified by GenBank Accession.No.NP_0054862 or NP_0054862.1 (SEQ ID NO: 17), while the mouse PD-L1 (hereinafter sometimes abbreviated to mPD-L1) is constituted by the amino acid sequence that is identified by GenBank Accession. No. NP_068693 or NP_068693.1 (SEQ ID NO: 18).

Examples of PD-L2 include human PD-L2 (hereinafter sometimes abbreviated to hPD-L2) and the corresponding immunoreceptors of mammalian. Herein, the mammals include a chimpanzee, cynomolgus monkey, mouse, rat, guinea pig, dog and pig. Particularly, the human PD-L2 is constituted by the amino acid sequence that is identified by GenBank Accession. No. NP_079515 or NP_079515.1, while the mouse PD-L2 (hereinafter sometimes abbreviated to mPD-L2) is constituted by the amino acid sequence that is identified by GenBank Accession. No. NP_067371 or NP_067371.1.

The extracellular domain of PD-1, particularly hPD-1, includes any region from the $1^{st}$ to $167^{th}$ domains of the hPD-1 amino acid sequence, wherein the binding activity to PD-L1 or PD-L2 is retained. In mPD-1, it includes any region from the 1st to 169th domains of the mPD-1 amino acid sequence, wherein the binding activity to PD-L1 or PD-L2 is retained.

The extracellular domain of PD-L1, particularly hPD-L1, includes any region from the 1st to 238th domains of the hPD-L1 amino acid sequence, wherein the binding activity to PD-1 is retained. In mPD-L1, it includes any region from the 1st to 237th domains of the mPD-L1 amino acid sequence, wherein the binding activity to PD-4 is retained.

The extracellular domain of PD-L2, particularly hPD-L2, includes any region from the 1st to 220th domains of the hPD-L2 amino acid sequence, wherein the binding activity to PD-1 is retained. In mPD-L2, it includes any region from the 1st to 219th domains of the mPD-L2 amino acid sequence, wherein the binding activity to PD-1 is retained.

When the multimer of the present invention is used as a pharmaceutical, test or diagnostic drug or a research reagent, the preferred PD-1 is hPD-1, and the preferred extracellular domain is present between the 25th and 145th domains of the hPD-1 amino acid sequence. In the case where the multimer is used as a test or diagnostic drug or a research reagent, mPD-1 is also preferable, and the preferred extracellular domains is present between the 25th and 145th domains of the mPD-1 amino acid sequence.

When the multimer of the present invention is used as a pharmaceutical, test or diagnostic drug or a research reagent, the preferred PD-L1 is hPD-L1, and the preferred extracellular domain is present between the 18th and 230th domains of the hPD-L1 amino acid sequence. In the case where the multimer is used as a test or diagnostic drug or a research reagent, mPD-L1 is also preferable, and the preferred extracellular domains is present between the 18th and 229th domains of the mPD-L1 amino acid sequence.

Some amino acids (preferably one to three, more preferably one amino acid) in the amino acid of each extracellular domains above may be substituted with other promer amino acids, in order to improve protein expression efficiency or refolding efficiency, or by other reasons.

Of the multimers of the present invention, a multimer with extracellular domains of PD-1 is preferably that in which 2 to 10 PD-1 extracellular domains are serially-concatenated through peptide linkers, more preferably that in which 2 to 6 domains are serially-concatenated, and further more preferably that in which 4 domains are serially-concatenated, i.e., a PD-1 tetramer. On the other hand, a multimer with extracellular domains of PD-L1 is preferably that in which 2 to 10 PD-L1 extracellular domains are serially-concatenated through peptide linkers, more preferably that in which 2 to 6 domains are serially-concatenated, and further more preferably that in which 4 domains are serially-concatenated, i.e., a PD-L1 tetramer.

The preferred peptide linker is a peptide with a length of 4 to 8 amino acids, and more preferably a peptide with a length of 6 amino acids. It is preferred that the peptide linker is free from antigenicity against human or has a therapeutically acceptable extent of antigenicity, when the multimer of the present invention is used as a pharmaceutical product.

Of the multimers of the present invention, a preferred hPD-1 tetramer is a polypeptide comprising the amino acid sequence of SEQ ID NO: 1, a preferred mPD-1 tetramer is a polypeptide comprising the amino acid sequence of SEQ ID NO: 3, a preferred hPD-L1 tetramer is a polypeptide comprising the amino acid sequence of SEQ ID NO 5, and a preferred mPD-L1 tetramer is a polypeptide comprising the amino acid sequence of SEQ ID NO: 7. The description of "Xaa" in the amino acid sequence shown in the sequence table means an unspecified amino acid.

Of the multimers of the present invention, a multimer wherein the extracellular domains of the cell surface functional molecule are bound through non-peptide linkers includes that in which the extracellular domains are extracellular domains of PD-1 bound through non-peptide linkers, and that in which the extracellular domains are extracellular domains of PD-L1 bound through non-peptide linkers. These multimers include those wherein a lysyl side chain in the peptide, which is added at the terminal of the extracellular domain of the cell surface functional molecule, is biotinylated with biotin ligase (e.g., BirA), followed by binding it to an avidin or a streptavidin derivative, or a proper carrier to which the avidin or the streptavidin derivative is added.

In the present invention, the "non-peptide linker" includes a substance in which a reaction group or interactional group, arbitrarily selected from biotin, succineimidyl derivatives, maleimide derivatives, hydrazide derivatives and the like, is added at both terminals of the spacer such as PEG in an arbitrary length, a substance in which cyanuric chloride is crosslinked to a hydroxyl group of cyclodextrin, and commercially available substances.

Even in the case where the multimer of the present invention is constituted by binding through non-peptide linkers, the number of the extracellular domains is preferably two to six, and more preferably four.

Polynucleotide Encoding the Multimer

In the present invention, "polynucleotide encoding the multimer" may be any kind, as long as containing a nucleotide sequence encoding the multimer of the present invention. Example of the polynucleotide include that wherein 2 to 10 polynucleotides encoding the extracellular domains of a wild-type cell surface functional molecule are serially-concatenated directly or through each polynucleotide encoding the peptide linker.

Further, examples of the polynucleotide include that wherein any amino acids (preferably one to three and more preferably one amino acid) in the polypeptide encoded by itself are modified by means of deletion, substitution or insertion with other amino acids, or combination thereof. For example, of the codons that correspond to the amino acids constituting the multimer of the present invention, Phe corresponds to TTT or TTC, Leu corresponds to TTA, TTG, CTT, CTC, CTA or CTG, Ile corresponds to ATT, ATC or ATA, Met corresponds to ATG, Val corresponds to GTT, GTC, GTA or GTG, Ser corresponds to TCT, TCC, TCA or TCG, Pro corresponds to CCT, CCC, CCA or CCG, Thr corresponds to ACT, ACC, ACA or ACG, Ala corresponds to GCT, GCC, GCA or GCG, Tyr corresponds to TAT or TAC, His corresponds to CAT or CAC, Gln corresponds to CAA or CAG, Asn corresponds to AAT or AAC, Lys corresponds to AAA or AAG, Asp corresponds to GAT or GAC, Glu corresponds to GAA or GAG, Cys corresponds to TGT or TGC, Trp corresponds to TGG, Arg corresponds to CGT, CGC, CGA or CGG, Ser corresponds to AGT or AGC, Arg corresponds to AGA or AGG, and Gly corresponds to GGT, GGC, GGA or GGG, respectively. Accordingly, the polynucleotide encoding the multimer of the present invention includes a polynucleotide wherein each codon corresponding to each amino acid in the amino acid sequence of the multimer of the present invention is arbitrarily combined. Particularly, there is a case where any amino acids are substituted by the corresponding codons, so as to enhance the expression efficiency of the multimer in the transformant of the present invention. The polynucleotide of the present invention may be any of genome DNA, cDNA, synthetic DNA, RNA and DNA-RNA hybrid.

Hereinafter, the polynucleotide encoding the multimer of the present invention may be abbreviated to "the polynucleotide of the present invention".

Examples of the polynucleotide encoding PD-1 include the hPD-1 cDNA and cDNAs derived from other mammals. Herein, the mammals include a chimpanzee, cynomolgus monkey, mouse, rat, guinea pig, dog and pig. Particularly, the hPD-1 cDNA is constituted by the nucleotide sequence identified by GenBank Accession. No. NM_005018 or NM_005018.1, while the mPD-1 cDNA is constituted by the nucleotide sequence identified by GenBank Accession. No. NM_008798 or NM_008798.1.

Examples of the polynucleotide encoding PD-L1 include the hPD-L1 cDNA and cDNA derived from other mammals. Herein, the mammals include a chimpanzee, cynomolgus monkey, mouse, rat, guinea pig, dog and pig. Particularly, the hPD-L1 cDNA is constituted by the nucleotide sequence identified by GenBank Accession. No. NM_014143, NM_014143.1 or NM_014143.2, while the mPD-L1 cDNA is constituted by the nucleotide sequence identified by GenBank Accession. No. NM_021893, NM_021893.1 or NM_021893.2.

Examples of the polynucleotide encoding PD-L2 include the hPD-L2 cDNA and cDNA derived from other mammals. Herein, the mammals include a chimpanzee, cynomolgus monkey, mouse, rat, guinea pig, dog and pig. Particularly, the hPD-L2 cDNA is constituted by the nucleotide sequence identified by GenBank Accession. No. NM_025239, NM_025239.1 or NM_025239.2, while the mPD-L2 cDNA is constituted by the nucleotide sequence identified by GenBank Accession. No. NM_021396 or NM_021396.1.

Examples of the polynucleotide of the present invention, wherein the extracellular domains of the multimer of the present invention are those of PD-1, includes a polynucleotide wherein 2 to 10 polynucleotides encoding the extracellular domains of the above hPD-1 (any region from the $1^{st}$ to $167^{th}$ domains of the amino acid sequence, retaining a binding activity to PD-L1 or PD-L2) are serially-concatenated directly or through each polynucleotide encoding a peptide linker, and a polynucleotide wherein 2 to 10 polynucleotides encoding the extracellular domains of the above mPD-1 (any region from the $1^{st}$ to $169^{th}$ domains of the amino acid sequence, retaining a binding activity to PD-L1 or PD-L2) are serially-concatenated directly or through each polynucleotide encoding a peptide linker.

Examples of the polynucleotide of the present invention, wherein the extracellular domains of the multimer of the present invention are those of PD-L1, include a polynucleotide wherein 2 to 10 polynucleotides encoding the extracellular domains of the above hPD-L1 (any region from the $1^{st}$ to $238^{th}$ domains of the amino acid sequence, retaining a binding activity to PD-1) are serially-concatenated directly or through each polynucleotide encoding a peptide linker, and a polynucleotide wherein 2 to 10 polynucleotides encoding the extracellular domains of the above mPD-L1 (any region from the $1^{st}$ to $237^{th}$ domains of the amino acid sequence, retaining a binding activity to PD-1) are serially-concatenated directly or through each polynucleotide encoding a peptide linker.

Likewise, examples of the polynucleotide of the present invention, wherein the extracellular domains of the multimer of the present invention are extracellular domains of PD-L2, include a polynucleotide wherein 2 to 10 polynucleotides encoding the extracellular domains of the above hPD-L2 (any region from the $1^{st}$ to $220^{th}$ domains of the amino acid sequence, retaining a binding activity to PD-1) are serially-concatenated directly or through each polynucleotide encoding a peptide linker, and a polynucleotide wherein 2 to 10 polynucleotides encoding the extracellular domains of the above mPD-L2 (any region from the $1^{st}$ to $219^{th}$ domains of the amino acid sequence, retaining a binding activity to PD-1) are serially-concatenated directly or through each polynucleotide encoding a peptide linker.

Herein, "each polynucleotide encoding a peptide linker" includes a polynucleotide with a length of 6 to 45 bases, which encodes a peptide linker with a length of 2 to 15 amino acids.

Of the polynucleotides of the present invention, a preferred polynucleotide with extracellular domains of PD-1 is that wherein 2 to 10 polynucleotides encoding the extracellular domains of the above hPD-1 (any region from the $25^{th}$ to $145^{th}$ domains of the amino acid sequence, retaining a binding activity to PD-L1 or PD-L2) are serially-concatenated directly or through each polynucleotide encoding a peptide linker, when the multimer of the present invention is used as a pharmaceutical, test or diagnostic drug, or a research reagent.

On the other hand, when the multimer of the present invention is used as a test or diagnostic drug or a research reagent, a preferred polynucleotide also includes that wherein 2 to 10 polynucleotides encoding the extracellular domains of the above mPD-1 (any region from the $25^{th}$ to $145^{th}$ domains of the amino acid sequence, retaining a binding activity to PD-L1 or PD-L2) are serially-concatenated directly or through each polynucleotide encoding a peptide linker.

Of the polynucleotides of the present invention, a preferred polynucleotide with extracellular domains of PD-L1 is that wherein 2 to 10 polynucleotides encoding the extracellular domains of the above hPD-L1 (any region from the $18^{th}$ to $230^{th}$ domains of the amino acid sequence, retaining a binding activity to PD-1) are serially-concatenated directly or through each polynucleotide encoding a peptide linker, when the multimer of the present invention is used as a pharmaceutical, test or diagnostic drug, or a research reagent.

On the other hand, when the multimer of the present invention is used as a test or diagnostic drug or a research reagent, a preferred polynucleotide also includes that wherein 2 to 10 polynucleotides encoding the extracellular domains of the above mPD-L1 (ay region from the $18^{th}$ to $229^{th}$ domains of the amino acid sequence, retaining a binding activity to PD-1) are serially-concatenated directly or through each polynucleotide encoding a peptide linker.

In the polynucleotide of the present invention, a more preferred polynucleotide is that encoding the amino acid sequence, wherein any amino acids (preferably one to three, and more preferably one amino acid) are substituted with proper amino acids, in order to improve the protein expression efficiency or refolding efficiency, or by other reasons.

In the polynucleotide of the present invention, the preferred number of polynucleotides encoding the extracellular domains constituting the multimer of the present invention is two to six, and more preferably four.

In the polynucleotide of the present invention, "each polynucleotide encoding a peptide linker" is preferably a polynucleotide with a length of 12 to 24 bases, which encodes a peptide linker with a length of 4 to 8 amino acids, and more preferably a polynucleotide with a length of 18 bases.

Of the polynucleotides of the present invention, a preferred polynucleotide encoding the hPD-1 tetramer is that encoding a polypeptide comprising the amino acid sequence of SEQ ID NO: 1, and a more preferred polynucleotide is that having the nucleotide sequence of SEQ ID NO: 2. A preferred polynucleotide encoding the mPD-1 tetramer is that encoding a polypeptide comprising the amino acid sequence of SEQ ID NO: 3, and a more preferred polynucleotide is that having the nucleotide sequence of SEQ ID NO: 4. A preferred polynucleotide encoding the hPD-L1 tetramer is that encoding a polypeptide comprising the amino acid sequence of SEQ ID NO: 5, and a more preferred polynucleotide is that having the nucleotide sequence of SEQ ID NO: 6. A preferred polynucleotide encoding the mPD-L1 tetramer is that encoding a polypeptide comprising the amino acid sequence of SEQ ID NO: 7, and a more preferred polynucleotide is that comprising the nucleotide sequence of SEQ ID NO: B. The denotation "n" in the nucleotide sequence shown in the sequence table means an unspecified base.

Expression Vector

The expression vector containing the polynucleotide encoding the multimer of the present invention (hereinafter sometimes abbreviated to the expression vector of the present invention) is prepared by connecting the polynucleotide encoding the multimer of the present invention to the downstream of a promoter in a proper expression vector. The preparation can be performed by a known method regarding genetic modification technique or a method analogous to the present Examples. Examples of the expression vector include *E. coli* expression vectors (e.g., pBR322, pBR325, pUC12, pUC13 and other commercially available ones), *Bacillus subtilis*-originated plasmids (e.g., pUB110, pTP5, pC194 and other commercially available ones), yeast expression vectors (e.g., pSH19, pSH15 and other commercially available ones), animal cell expression vectors (e.g., pA1-11, pXT1, pRc/CMV, pRc/RSV, pcDNAI/Neo and other commercially available ones), bacteriophages (e.g., λ phage) and animal viruses (e.g., retrovirus, vaccinia virus and baculovirus).

Transformant

Examples of the host for the transformant of the present invention include *Escherichia* strains, *Bacillus* strains, yeasts, insect cells, insects and animal cells.

Examples of the *Escherichia* strains include *Escherichia coli* (e.g., K12•131-11, JM103, JA221, HB101 and C600).

Examples of the *Bacillus* strains include *Bacillus subtilis* (e.g., M1114 and 207-21).

Examples of the yeasts include *Saccharomyces cerevisiae, Schizosaccharomyces pombe* and *Pichia pastoris*.

Examples of the insect cells include Sf cells (e.g., Sf9 cell and Sf21 cell), MG1 cells and High Five TM cells when the virus is AcNPV. When the virus is BmNPV, BmN cells are used.

Examples of the insects include silkworm larvae.

The animal cells may be any kind, as long as being temporarily, continuously or steadily transformed by the expression vector of the present invention. Preferred animal cells are those steadily transformed, and capable of expressing the multimer of the present invention continuously or steadily. Examples of the animal cells include COS1 cells, COS7 cells, CHO cells, CHO-K1 cells, HEK293 cells, U937 cells, Jurkat cells, Hela cells, Daudi cells, K562 cells, mouse L cells, NIH3T3 cells, A549 cells, BHK-21 cells, SRT-3A cells, HepG2 cells, HUVEC cells, PC12 cells, RAW264.7 cells, THP-1 cells and L929 cells.

The transformant of the present invention is prepared by transforming the host with the expression vector of the present invention. The transformation can be performed by a known method or a method analogous to the present Examples, depending on a type of the host. The hosts described above can be obtained from depository institutions.

Method for Production of Polynucleotide

The polynucleotide encoding the multimer of the present invention can be prepared by a known method or a method analogous to the present Examples. For example, it is prepared by PCR-amplifying method, using synthetic DNA primers encoding each part of the extracellular domains of the cell surface functional molecule constituting the multimer of the present invention. The PCR method can be performed by a known method or a method analogous to the present Examples. The polynucleotide encoding the multimer of the present invention is obtained in a necessary quantity by introducing a vector containing the polynucleotide into a proper host fox proliferation.

Method for Production and Purification of Multimer

The multimer of the present invention is prepared by the method which comprises culturing the above transformant, and producing it in a bacteria form or a cell or secreting it. For example, when the multimer of the present invention is extracted from a cultured bacteria, a method to be applied is: the bacterias collected by a known method are suspended in a proper buffer solution, the bacterias or the cells are destroyed by ultrasonic waves, lysozyme and/or freeze-thaw, and the resultant suspension is subjected to centrifugation or filtration to obtain a crude extract of soluble protein. The buffer solution may contain a protein denaturant such as urea and guanidine hydrochloride, and a surfactant such as TRITON® X-100.

Separation and purification of the multimer of the present invention contained in the resultant crude extract of soluble protein can be performed by a known method or a method analogous to the present Examples. For example, it is conducted by a method based on solubility such as salting-out and solvent precipitation, a method based on difference of molecular weights such as dialysis, ultrafiltration, gel filtration and SDS-polyacrylamide gel electrophoresis, a method based on difference of electric charges such as ion exchange chromatography, a method based on specific affinity such as affinity chromatography, a method based on difference of hydrophobicity such as hydrophobic chromatography and reverse phase chromatography, and a method based on difference of isoelectric points such as isoelectric focusing electrophoresis. It can also be performed in combination of these methods.

When the multimer of the present invention prepared by the above method is a free body, the free body is able to be converted into a salt by a known method or a method analogous thereto.

The multimer of the present invention is also prepared by in vitro translation, using the above polynucleotide of the present invention as a template, using a cell-free protein translation system using rabbit reticulocyte lysate, wheat germ lysate, *E. coli* lysate and the like. It is also prepared by a cell-free transcription/translation system, using the polynucleotide of the present invention as a template.

The multimer of the present invention can also be expressed as a fusion protein with other proteins or a tag (e.g., Fc domain of an antibody, glutathione S transferase, protein A and hexahistidine). The fusion protein is purified with affinity chromatography and/or cleaved with a proper protease (e.g., enterokinase and thrombin), enabling efficient purification.

Application to Medication

Since the immunotherapy is a method for activating immune responses that a human essentially has, a patient has less stress. Therefore, it is expected to reduce side effects incurred by a conventional medication therapy. Particularly, since the chemotherapy for cancer treatment inflicts great burdens on the patient, the method is expected as a therapy to reduce burdens on a cancer patient.

Immunostimulation can be performed by a method for activating immune responses of a certain kind of a T-cell. An activation signal necessary for the activation via a T-cell receptor complex is usually suppressed by an immunosuppression receptor to be conjugated therewith. Therefore, suppressing function of the immunosuppression receptor will be an effective means for activation of a T-cell or immunostimulation.

It is presumed that PD-1 relating to the present invention functions as an immunosuppression receptor in a T-cell. Accordingly, each multimer of the present invention in the extracellular domains of PD-1, PD-L1 or PD-L2, or each pharmaceutical product containing it as an active ingredient is used for prevention and/or treatment of cancer or cancer matastasis, and further used for prevention and/or treatment of immune deficiency syndrome and infectious diseases.

Examples of the cancer or tumor, to which prevention and/or therapeutic effects are expected by administration of each multimer of the present invention comprising the extracellular domains of PD-1, PD-L1 or PD-L2 or administration of the medicine containing it as an active ingredient, include tongue cancer, gingival cancer, malignant lymphoma, malignant melanoma, maxillary cancer, nasal cancer, nasal cavity cancer, laryngeal cancer, pharyngeal cancer, glioma, meningioma, glioma, neuroblastoma, thyroid papillary adenocarcinoma, thyroid follicular carcinoma, medullary thyroid cancer, primary lung cancer, squamous cell carcinoma, adenocarcinoma, alveolar cell carcinoma, large cell undifferentiated carcinoma, small cell undifferentiated carcinoma, carcinoid, testicular tumor, prostate cancer, breast cancer (e.g., papillary adenocarcinoma, comedecarcinoma, mucinous carcinoma, medullary carcinoma, lobular carcinoma, scirrhus sarcoma and metastatic tumor), breast Paget's disease, breast sarcoma, bone tumor, thyroid cancer, gastric cancer, liver cancer, acute myeloid leukemia, acute promyelocytic leukemia, acute myelomonocytic leukemia, acute monocytic leukemia, acute lymphocytic leukemia, acute undifferentiated leukemia, chronic myeloid leukemia, chronic lymphocytic leukemia, adult T-cell leukemia, malignant lymphoma (e.g., lymphosarcoma, reticulum cell sarcoma and hodgkin's disease), multiple myeloma, primary macroglobulinemia, infantile leukemia, esophageal cancer, gastric cancer, gastric/colon leiomyosarcoma, gastric/intestinal malignant lymphoma, pancreatic/gallbladder cancer, duodenal cancer, colorectal cancer, primary liver cancer (e.g., hepatocellular carcinoma and cholangiocellular carcinoma), hepatoblastoma, uterine carcinoma in situ, uterine cervix squamous cell carcinoma, uterine adenocarcinoma, uterine gland squamous cell carcinoma, uterus body adenocancroid, uterine sarcoma, uterus carcinosarcoma, uterus invasive mole, syncytioma malignum uteri, malignant uteri melanoma, ovarian cancer, mesodermal mixed tumor, kidney cancer, renal pelvic transitional cell carcinoma, ureteral transitional cell carcinoma, papillary carcinoma of the bladder, bladder transitional cell carcinoma, squamous cell carcinoma of the urethra, adenocarcinoma of the urethra, Wilm's tumor, rhabdomyosarcoma, fibrosarcoma, osteodarcoma, chondrosarcoma, synovial sarcoma, myxosarcoma, liposarcoma, Ewing's sarcoma, skin squamous cell cancer, epithelioma basocellulaire, skin Bowen's disease, skin Paget's disease, cutaneous malignant melanoma, malignant mesothelial cancer, metastatic adenocarcinoma, metastatic squamous cell carcinoma, metastatic sarcoma and mesothelioma (e.g., pleural mesothelioma, peritoneal mesothelioma and pericardial mesothelioma).

The effect of each multimer of the present invention comprising the extracellular domains of PD-1, PD-L1 or PD-L2, or effect of the medicine containing it as an active ingredient, can be evaluated in an animal tumor model. Examples of the animal tumor model include a model in which a proper number of SaiN tumor cells is subcutaneously implanted to a A/J mouse (WO 2000/037504), a model in which a proper number of B16 melanoma cells is subcutaneously implanted to a C57BL/6 mouse (International Immunology, 2004, No. 17, No. 2, pp. 133-144) or a proper number of MC38 colorectal cancer cells is subcutaneously implanted to a C57BL/6 mouse (WO 2006/121168), a model in which a proper number of P815 mast cell tumor-derived cells is subcutaneously implanted to a DBA/2 mouse (Proc Natl Acad Sci USA., 2002, Vol. 99, No. 19, pp. 12293-7), and a model in which a proper number of J558L myeloma cells is subcutaneously implanted to a Ba1b/C mouse (Proc Natl Acad Sci USA., 2002, Vol. 99, No. 19, pp. 12293-7) or a proper number of CT26 colorectal cancer cells is subcutaneously implanted to a Ba1b/C mouse (International Immunology, 2004, N. 17, No. 2, pp. 133-144). The implanted cancer cells are grown for a proper period, to which a proper amount of the multimer of the present invention is administered once or several times, and a size of the tumor mass formed by the cancer cells is measured. This procedure enables us to evaluate the anticancer or antitumor activity. The evaluation can also be done using a model in which non-small-cell lung cells (NSCL), rectal carcinoma cells or the like, which are derived from a patient, are subcutaneously implanted to a SCID mouse with human T-cells implanted (J. Surgical res., 1996, Vol. 61, pp. 282-288).

Examples of the immune deficiency syndrome, to which prevention and/or therapeutic effects are expected by administration of each multimer of the present invention in the extracellular domains of PD-1, PD-L1 or PD-L2 or administration of the medicine containing it as an active ingredient, include acquired immunodeficiency syndromes (AIDS) caused by human immunodeficiency virus infection (opportunistic infections, e.g., candida esophagitis, carinii pneumonia, toxoplasmosis, tuberculosis, mycobacterium-avium complex infection, cryptosporidiosis, cryptococcal meningitis, cytomegalovirus infectious disease and progressive multifocal leukoencephalopathy), and immune deficiency accompanying severe diseases (e.g., cancer, aplastic anemia, leukemia, myelofibrosis, renal failure, diabetes, liver diseases and splenic diseases) and primary immune deficiency syndromes.

Further, prevention and/or therapeutic effects of various infectious diseases are expected by administration of each multimers of the present invention comprising the extracellular domains of PD-1, PD-L1 or PD-L2 or administration of the medicine containing it as an active ingredient. Particularly, it is presumed that a certain kind of viruses exploits an immunosuppression receptor as one of the methods for escaping from immune defense of the infected host (Journal Experiment) Medicine, 2000, Vol. 191, No. 11, pp. 1987-1997). Virus infection is partly caused by such an escape function of a virus, so that it is considered to be achievable to increase immune response against a virus in the immune cell, by means of administration of the multimer of the present invention or the medicine containing it as an active ingredient.

Examples of the infectious disease include those caused by an influenza virus (e.g., A-type (H1N1, H2N2, H3N2, H5N1 and H9N1), B-type and C-type) or an influenza virus that infects to other mammals or birds, cold virus (e.g., adenovirus, enterovirus and rhinovirus), human hepatitis virus (e.g., hepatitis type B, C, A and E viruses), human retrovirus, human immunodeficiency virus (e.g., HIV1 and HIV2), human T-cell leukemia virus or human T-lymphogenic virus (e.g., HTLV1 and HTLV2), herpes simplex virus type I or type II, Epstein-Barr virus, cytomegalovirus, varicella-herpes virus, human herpes virus (e.g., human herpes virus 6), polio virus, measle virus, rubella virus, Japanese encephalitis virus, mumps virus, norovirus, virus developing severe acute respiratory syndromes (SARS), Ebola virus and west Nile virus.

It is also considered that the present medicine is effective for infections caused by, e.g., pathogenic protozoa (e.g., trypanosome, malaria and *toxoplasma*), bacteria (e.g., *mycobacterium, salmonella* and *listeria*) and fungi (e.g., candida).

Toxicity

Since the antigenicity and toxicity of the multimer of the present invention is fairly low, it is safe enough for medicinal use.

Application to Medical Supplies

The multimer of the present invention is used as a single drug or as a pharmaceutical composition mixed it with various pharmacologically acceptable formulations.

The pharmaceutical composition is usually administered by a parenteral administration route, but can be orally administered. Examples of the parenteral administration include administration by injection, and percutaneous, transmucosal, transnasal and transpulmonary administrations.

The injection includes a solution, a suspension, and a solid injection that is dissolved or suspended in a solvent before use.

The injection is used after one or more active ingredients are dissolved, suspended or emulsified in a solvent. Examples of the solvent include water-soluble solvents (e.g., distilled water, physiological saline and Ringer's solution), oil solvents (e.g., vegetable oils such as olive oil, sesame oil, cotton oil and corn oil, and alcohols such as propylene glycol, polyethylene glycol and ethanol), and combination thereof.

Further, the injection may contain a stabilizer (e.g., human serum albumin), solubilizing agent (e.g., polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate), suspending agent (e.g., surfactants such as stearyl triethanolamine, sodium lauryl sulfate, lauryl aminopropionic acid, lecithin, benzalkonium chloride, benzethonium chloride and glyceryl monostearate; hydrophilic polymers such as polyvinyl alcohol, polyvinyl pyrrolidone, sodium carboxymethyl cellulose, methyl cellulose, hydroxymethyl cellulose, hydroxyethyl cellulose and hydroxypropyl cellulose; polysorbates; and polyoxyethylene hardened castor oil), emulsifier, soothing agent (e.g., benzyl alcohol), tonicity agent (e.g., sodium chloride, glycerin, D-mannitol, D-sorbitol and glucose), buffer, preservative (e.g., methylparaben, propylparaben, benzyl alcohol, chlorobutanol and phenol), antiseptic (e.g., paraoxybenzoic esters, chlorobutanol, benzyl alcohol, phenethyl alcohol, dehydroacetic acid and sorbic acid), antioxidant (e.g., sulfite and ascorbate) and dispersant (e.g., Polysorbate 80, Polyoxyethylene hardened castor oil 60, ethylene glycol, carboxymethyl cellulose and sodium alginate).

These injections are prepared by known methods in the formulation technology field, such as by a method described in Japanese Pharmacopoeia. They are prepared, for example, through a sterilization process at the final stage, or by aseptic manipulation. It is also possible to use an aseptic solid formulation, such as a freeze dry product, wherein the aseptic solid formulation is prepared and dissolved in aseptic or sterilized distilled water for injection or other solvents before use.

These parenteral solutions are supplied in a vessel with a standard capacity, such as a plastic or glass vial, ampule, syringe and injector, or in a vessel with a large capacity, such as a bottle.

The dosage of the multimer of the present invention varies depending on age, weight, symptom, therapeutic efficacy, dosing regimen and/or treatment time. Generally, it is administered by a parenteral route (preferably intravenous administration) in an amount of 1 ng to 100 mg per time, from once a couple of days, once 3 days, once 2 days, once a day to a couple of times a day, in the case of an adult, or continuously administered by intravenous administration from 1 to 24 hours a day. Since the dosage is affected by various conditions, an amount less than the above dosage may sometimes works well enough, or higher dosage may be required in some cases.

The injection for parenteral administration includes all injections, and also includes intravenous fluids. For example, it includes intramuscular injections, subcutaneous injections, intradermal injections, intraarterial injections, intravenous injections, intraperitoneal injections, injections to spinal cavity, and intravenous drops.

The multimer of the present invention may be administered in combination with other drugs for (1) complement and/or enhancement of prevention and/or therapeutic efficacy of the preventive and/or therapeutic drug of the present invention, (2) dynamics, absorption improvement, dosage reduction of the preventive and/or therapeutic drug of the present invention, and/or (3) reduction of the side effects of the preventive and/or therapeutic drug of the present invention.

A concomitant medicine comprising the multimer of the present invention and other drug may be administered as a combination preparation in which both components are contained in a single formulation, or administered as separate formulations. The administration by separate formulations includes simultaneous administration and administration with some time intervals. In the case of the administration with some time intervals, the multimer of the present invention can be administered first, followed by another drug, or another drug can be administered first, followed by the multimer of the present invention. The administration method of the respective drugs may be the same or different.

The dosage of the other drug can be properly selected, based on a dosage that has been clinically used. The compounding ratio of the multimer of the present invention and the other drug can be properly selected according to age and weight of a subject to be administered, administration method, administration time, disorder to be treated, symptom and combination thereof. For example, the other drug may be used in an amount of 0.01 to 100 parts by mass, based on 1 part by mass of the multimer of the present invention. The other drug may be a combination of two or more kind of arbitrary drugs in a proper proportion. The other drug that complements and/or enhances the preventive and/or therapeutic efficacy of the multimer of the present invention includes not only those that have already been discovered, but those that will be discovered in future, based on the above mechanism.

Diseases on which this concomitant use exerts a preventive and/or therapeutic effect are not particularly limited. The concomitant medicine can be used for any diseases, as long as it complements and/or enhances the preventive and/or therapeutic efficacy of the multimer of the present invention.

Particularly, since the multimer of the present invention exhibits an effect of stimulating or proliferating lymphoid cells, the concomitant use is able to reduce a dosage of chemotherapeutics commonly used or an irradiation dosage in radio therapy. This results in suppression of side effects that accompany with chemotherapy and radio therapy.

The multimer of the present invention can be used with an existing chemotherapeutic concomitantly or in a mixture form. Examples of the chemotherapeutic include an alkylation agent, nitrosourea agent, antimetabolite, anticancer antibiotics, vegetable-origin alkaloid, topoisomerase inhibitor, hormone drug, hormone antagonist, aromatase inhibitor, P-glycoprotein Inhibitor, platinum complex derivative, other immunotherapeutic drugs and other anticancer drugs. Further, it can be used with a cancer treatment adjunct, such as a leucopenia (neutrophenia) treatment drug, thrombocytopenia treatment drug, antiemetic and cancer pain intervention drug, concomitantly or in a mixture form.

The multimer of the present invention can be used with other immunomodulators concomitantly or in a mixture form. Examples of the immunomodulator include various cytokines. Examples of the cytokines that stimulates immune responses include GM-CSF, M-CSF, G-CSF, interferon-α, β, or γ, IL-1, IL-2, IL-3 and IL-12.

The concomitant use of the multimer of the present invention and a cancer antigen is able to give an additive or synergetic enhancement effect. Examples of the cancer antigen include HLA-A1 and HLA-A2 derived peptides derived from MAGE-1 or MAGE-3 of malignant melanoma, MART-1 and gp100, HER2/neu peptide of breast cancer and ovarian cancer, MUC-1 peptide of adenocarcinoma and NY-ESC-1 of metastatic cancer.

The multimer of the present invention can be used with an antiviral agent, antibiotic preparation, antimicrobial or visceral mycosis therapeutic agent concomitantly or in a mixture form. Examples of the antiviral agent include anti-HIV drags, anti-influenza virus drugs, anti-herpes virus drugs, interferon-α or β, and various immunoglobulins. Herein, examples of the anti-HIV drugs include a reverse transcriptase inhibitor (e.g., AZT, ddI, 3TC and d4T), protease inhibitor (e.g., saquinavir mesylate, ritonavir, nelfinavir mesylate, amprenavir, delavirdine mesylate, saquinavir, and lopinavir/ritonavir), and CCR5 receptor antagonist. Examples of the anti-influenza drugs include various influenza vaccines, oseltamivir phosphate, zanamivir hydrate and amantadine hydrochloride.

The multimer of the present invention can be concomitantly used with a virus or vaccine of a pathogen, or formulated therewith. Examples of the vaccine include polio, measles, Japanese encephalitis, BCG, triple, mumps, chickenpox, influenza, hepatitis type A, hepatitis type B and cholera vaccines.

Use as Test or Diagnostic Drug

Since the multimer of the present invention binds to its ligand molecule strongly and specifically, the labeling agent thereof is able to be used as a test or diagnostic drug or a research reagent for diseases in which the cell surface functional molecule or the ligand molecule is involved.

Examples of the labeling agent that can label the multimer of the present invention include radioisotopes, enzymes, fluorescent materials, luminous materials, ultraviolet absorption materials and spin-labeling materials.

When the multimer of the present invention is used in an enzyme-linked immunosorbent assay (EIA) method, it can be used by labeling it with enzymes, such as alkali phosphatase, β-galactosidase, peroxydase, microperoxydase, glucose oxydase, glucose-6-phosphate dehydrogenase, acetylcholinesterase, malate dehydrogenase and luciferase.

When the multimer of the present invention is used in a radioimmunoassay (RIA) method, it can be used by labeling it with a radioisotope, such as $^{131}I$, $^{125}I$, $^{99m}Tc$, $^{35}S$, $^{32}P$, $^{14}C$ and $^{3}H$.

When the multimer of the present invention is used in a fluorescence immunoassay (FIA) method, it can be used by labeling it with a fluorescent material, such as fluorescein, dansyl, fluorescamine, coumarin, naphthylamine, fluorescein isothiocyanate, rhodamine, rhodamine X isothiocyanate, sulforhodamine 101, Lucifer yellow, acridine, acridine isothiocyanate, riboflavin and the derivatives, and europium (Eu).

When the multimer of the present invention is used in a chemiluminescent immunoassay (CLIA) method, it can be used by labeling it with a luminous material, such as luminol derivatives, e.g., luciferin, isoluminol, luminol, aminoethyl isoluminol, aminoethylethyl isoluminol, aminopropyl isoluminol, aminobutyl isoluminol and aminohexylethyl isoluminol; luciferin; lucigenin; and bis(2,4,6-trifluorophenyl) oxalate.

When the multimer of the present invention is used in an ultraviolet absorption method, it can be used by labeling it with a substance that has absorption in a wavelength of ultraviolet rays, such as phenol, naphthol, anthracene and derivatives thereof.

When the multimer of the present invention is used in an electron spin resonance (ESR) method, it can be used by labeling it with a spin labeling agent represented by a compound having an oxyl group, such as 4-amino-2,2,6,6-tetramethylpiperidine-1-oxyl, 3-amino-2,2,5,5-tetramethylpyrrolidine-1-oxyl, 2,6-di-t-butyl-α-(3,5-di-t-butyl-4-oxo-2,5-cyclohexadien-1-ylidene)-p-tolyl oxyl.

Further, the multimer of the present invention can be labeled with any labeling agents that are commonly used in the field.

In order to bind the above labeling agent to the multimer of the present invention, known labeling methods, which are commonly performed in EIA, RIA, FIA and the like, are applied, such as those described in "Medical Chemistry Experimental Course, $1^{st}$ Ed., Vol. 8, Edited by U. Yamamura, published by Nakayama Bookstore, 1971; Illustrated Fluorescent Antibody, $1^{st}$ Ed., written by A. Kawao, published by Softscience, 1983; and Enzyme-linked immunoassay, $2^{nd}$ Ed., compiled by E. Ishikawa, T. Kawai and K. Mural, published by Igakushoin, 1982".

Of such labeling methods, a preferred method includes that exploits a reaction between avidin (or sreptavidin) and biotin. In the case of exploiting the reaction between avidin (or streptavidin) and biotin, a method for binding biotin with the multimer of the present invention includes a method for reacting a commercially available biotinylating agent (e.g., an agent prepared by binding biotin to which a succineimide group (e.g., NHS-biotin) is introduced or N-hydroxysuccinic acid imide (NHS) with biotin through a spacer) with an amino group in protein (Journal of Biological Chemistry, 1989, Vol. 264, pp. 272-279); a method for reacting a commercially available biotin-HPDP (N-[6-(biotinamide)hexyl]-3'-(2'-pyridylthio)propione amide) or N-iodoacetyl-N-biotinylhexylenediamine with a thiol group in protein (Ann. New York Acad. Sci., 1975, Vol. 254, No. 203); or a method for reacting biotin, to which a hydrazine group is introduced, with an aldehyde group in aldehyded protein (Biotech. Apple. Biochem., 1987, Vol. 9, pp. 488-496). A method analogous to the Examples can be performed as well.

EXAMPLES

The present invention is described in detail below by way of Examples and Biological Examples, but the present invention is not limited thereto.

Example 1

Formulation of Expression Vector for Extracellular Domain

A DNA fragment encoding a hPD-1 extracellular domain (a domain from $25^{th}$ to $145^{th}$ in the amino acid sequence of hPD-1) was obtained by PCR reaction (0.05 U/μL of ExTaq (Takara Shuzo Co., Ltd.), 0.5 μM of each primer; at 94° C. for one minute and at 72° C. for two minutes, 35 cycles) using hPD-1 cDNA (see Non-Patent Document 1) subcloned into pBluescript as a template and a forward primer (SEQ ID NO:9) and a reverse primer (SEQ ID NO:10). The DNA fragment was purified using a QIAquick Gel Extraction Kit (Qiagen), and the fragment digested by restriction enzymes EcoRI and SaiI was cloned into a pET expression vector.

Further, a TGC codon corresponding to cysteine at the 93$^{rd}$ position in the amino acid sequence was converted into TCC corresponding to serine, by single-point mutation using a QuikChange™ Site-Directed Mutagenesis Kit (Stratagene). The mutation was inserted in accordance with the method described in the attached document of the kit.

Likewise, a DNA fragment encoding a mPD-1 extracellular domain (a domain from 18$^{th}$ to 230$^{th}$ in the amino acid sequence of hPD-L1) was obtained by the above PCR reaction using mPD-1 cDNA (see EMBO Journal, 1992, Vol. 11, No. 11, pp. 3887-3895) as a template and a forward primer (SEQ ID NO:11) and a reverse primer (SEQ ID NO:12). It was cloned into an expression vector in the same manner as above. Further, the TGC codon corresponding to cysteine at the 83$^{rd}$ position in the amino acid sequence was converted into AGC corresponding to serine in the same manner as above.

Likewise, a DNA fragment encoding a hPD-L1 extracellular domain (a domain from 18$^{th}$ to 230$^{th}$ in the amino acid sequence of hPD-L1) was obtained by the above PCR reaction using hPD-L1 cDNA (see Non-Patent Document 6) as a template and a forward primer (SEQ ID NO:13) and a reverse primer (SEQ ID NO:14). It was cloned into an expression vector in the same manner as above.

A DNA fragment encoding a mPD-L1 extracellular domain (a domain from 18$^{th}$ to 229$^{th}$ in the amino acid sequence of mPD-L1) was obtained, by the above PCR reaction using mPD-L1 cDNA (see Non-Patent Document 6) as a template and a forward primer (SEQ ID NO:15) and a reverse primer (SEQ ID NO:16). It was cloned into an expression vector in the same manner as above. Further, the TGC codon corresponding to cysteine at the 113$^{rd}$ position in the amino acid sequence was converted into AGC corresponding to serine in the same manner as above.

Example 2

Expression of Extracellular Domain

Each expression vector prepared in Example 1 was introduced into *E. coli* Rosetta (DE3) pLys by electroporation, and each colony grown in a selective medium was cultured in a TB medium (0.4% glycerol, 50 μg/mL of ampicillin, 34 μg/mL of chloramphenicol, 50 μg/mL of carbenicillin (Wako Pure Chemical Industries) and a terrific broth (Difco) containing a drop of defoamer) for 5 hours. 1 mM of Isopropyl-β-D(−)thiogalactopyranoside (IPTG) was added thereto, which was then cultured for 10 hours.

After collecting cultured bacteria, it was washed with 10 mM of tris-hydrochloric acid (ph 8.0), suspended in a suspending buffer solution (10-100 mM of tris-hydrochloric acid (pH 7.0 to 8.0), 15-25% w/v sucrose, 0.5-2.0 mM of Na$_2$EDTA (pH 8.0), 0.05-0.15% sodium azide and 5-15 mM of dithiothreitol (hereafter abbreviated to DTT)), and treated with a proper amount of lysozyme at room temperature for 1 hour. A lysis buffer (10-100 mM of tris-hydrochloric acid (pH 7.0 to 8.0), 0.5-1.5% v/v of TRITON®-X100, 0.5-1.0% w/v of Sodium deoxycholate, 50-200 mM of sodium chloride, 0.05-0.15% sodium azide, 5-15 mM of DTT and 0.5-2.0 mM of Na$_2$EDTA (pH 8.0)) was added to the suspension, which was then mixed and intensely shaken at room temperature for 1 hour, followed by letting it stand overnight at −80° C. After unfreezing, a DNase treatment solution (1 mg of DNaseI and 30-90 mM of magnesium chloride) was added thereto, and which was intensely shaken for 8 hours.

After centrifugation, the recovered inclusion precipitate was washed with a wash buffer (10-100 mM of tris-hydrochloric acid (pH 7.0 to 8.0), 0.1-1.5% TRITON® X-100, 50-200 mM of sodium chloride, 0.05-0.15% sodium azide, 0.5-1.5 mM of DTT and 0.5-1.5 mM of Na$_2$EDTA (pH 8.0)), and homogenized. It was washed with the wash buffer twice, further rinsed, suspended in a urea-guanidine solution (15-30 mM of MES (pH 5.5 to 6.5), 5-15 mM of Na$_2$EDTA (pH 8.0), 0.5-2.0 M of urea, 4-6 M of guanidine hydrochloride and 0.5-1.5 mM of DTT), and homogenized. After centrifugation, the supernatant solution was collected. The final concentration of DTT was adjusted to 20-60 mM, and the solution was let stand at 37° C. for 1 hour.

In order to allow the respective extracellular domain prepared by the above method to be refolded, the above solution was let stand in a refolding buffer (0.5-1.0 M of arginine hydrochloride, 60-150 mM of tris-hydrochloric buffer solution (pH 8.0), 0.1-1.0 M of sucrose, 0.1-1.0 M of guanidine hydrochloride, 0.3-0.7 mM of reduced glutathione, 0.03-0.06 mM of oxidized glutathione, 0.5-3.0 mM of Na$_2$EDTA (pH 8.0) and 0.2-0.7 mM of phenylmethanesulfonyl fluoride) overnight at 4° C. It was dialyzed with a 0.1-0.3 M of urea solution at 4° C., followed by with a 5-15 mM of tris-hydrochloric buffer solution (pH 7.0 to 8.0) for 3 times, and then purified with a DE52 anion exchange column (Whatman International Ltd.) and a Q-Sepharose column (Amersham Biosciences) (see FIGS. 1A and 1D).

Further, it was purified with gel filtration column chromatography (Superdex 200) under a gradient of sodium chloride (10-30 mM of tris-hydrochloric buffer solution (pH 7.0 to 8.0)) (see FIG. 1B and FIG. 1E). As for each concentration in Examples, optimum concentration in compliance with a known method in the field of protein expression was adopted.

Each purified extracellular domain was subjected to circular dichroism analysis (CD analysis) by a common method. The results are shown in FIG. 1.

In FIG. 1, (A) and (D) show elution patterns of the extracellular domain of mPD-1 and that of mPD-L1 by anion exchange column chromatography, respectively. (B) and (E) show elution patterns of the extracellular domain of mPD-1 and that of mPD-L1 by gel filtration column chromatography, respectively. (C) and (F) show the results of circular dichroism analysis for the extracellular domain of mPD-1 and extracellular domain of mPD-L1, respectively.

Results

As a result of CD analysis, it was confirmed that each extracellular domain was refolded, based on the spectrum unique to a β-sheet structure (see FIGS. 1C and 1F).

In the same manner, the extracellular domain of hPD-1 and that of hPD-L1 were purified and refolded.

Example 3

Tetramerization of Extracellular Domain

Each extracellular domain prepared in Example 2 was dialyzed with 5-20 mM of tris-hydrochloric buffer solution (pH 7.0 to 8.0). After dialysis, 200-600 mM of d-biotin (30 μL), a solution A (0.5 M of bicin (pH 8.0-8.5); 40 μL), a solution B (100 mM of adenosine triphosphate, 100 mM of magnesium acetate and 200 mM of d-biotin; 40 μL) and 1 mg/mL of BirA enzyme (2.5 μL; CosmoBio) were added to the protein preparation solution (300 μL). The mixture solution was reacted overnight at room temperature, and dialyzed with 10 mM of tris-hydrochloric buffer solution (pH 8.0). R-PE-streptoavidin (Becton, Dickinson and Company) was added thereto, which was then purified with Sephadex gel. As for each concentration in Examples, optimum concentration in compliance with a known method in the field of protein expression was adopted.

Example 4

Binding Analysis with Flow Cytometry

The mPD-1 tetramer (50 μL) prepared in Example 3 was added to $5\times10^5$ of hPD-L1-expressing P815 cells (hereafter, sometimes abbreviated to P815/hPD-L1 cells, which were prepared in accordance with a method described in Non-Patent Document 8), which was then let stand on ice in a dark room for 20 minutes. They were washed with a saline solution 3 times, and R-PE-streptoavidin (100 μL) was added thereto. They were let stand on ice in a dark room for 20 minutes more, washed twice, suspended in PBS (200 μL, 1% paraformaldehyde), and added with a saline solution (500 μL). The resultant cell suspension was analyzed with flow cytometer (FACScalibur) (Becton, Dickinson and Company). An isotype matched antibody was used as a control.

The analysis of the mPD-L1 tetramer prepared in Example 3 was performed in the same manner as above, using mPD-1-expressing IIA. 6 cells (hereafter, sometimes abbreviated to an IIA. 6/mPD-1 cell). The 11A. 6/mPD-1 cells were prepared in accordance with a method described in Proc Natl Acad Sci USA., 2001, Vol. 98, No. 24, pp. 13866-71. The results are shown in FIG. 2.

In FIG. 2, (A) and (E) show the mPD-1 monomer and mPD-L1 monomer binding to each P815/hPD-L1 cell, and (C) and (G) show the mPD-1 tetramer and mPD-L1 tetramer binding to each P815/hPD-L1 cell. (B) and (F) show the mPD-1 monomer and mPD-L1 monomer binding to each P815 cell, and (D) and (H) show the mPD-1 tetramer and mPD-L1 tetramer binding to each P815 cell. In each figure, a heavy line shows each monomer or each tetramer, while a thin line shows addition of control, i.e., R-PE-streptoavidin.
Results The mPD-1 tetramer and mPD-L1 tetramer gave remarkable increase in binding activity, compared to each monomer (see FIGS. 2C and 2G). Likewise, the hPD-1 tetramer gave remarkable increase in avidity, compared to the monomer.

Example 5

Surface Plasmon Resonance Analysis

Surface plasmon resonance analysis was carried out with BIAcore (Biacore). 20 μg/ml, of mPD-1/Fc (10 mM of acetic buffer solution (pH 4.0); R&D systems) was attached to the CMS sensor chip, blocked with 1 M of ethanolamine-hydrochloric buffer solution (pH 8.5), followed by washed with 10 mM of glycin-hydrochloric buffer solution (pH 1.5). 100, 50 and 25 μg/mL of the mPD-L1 tetramer and 100, 50, 25, 12.5 and 6.25 μg/mL of the mPD-L1 monomer were injected at a flow rate of 10 μL/min to measure the binding activity to mPD-1/Fc. The Kd value was calculated with the analysis software provided with BIAcore. The measurement and analysis of the hPD-1 tetramer and mPD-1 tetramer were performed in the same manner as above (hPD-L1/Fc or mPD-L1/Fc was used as a ligand). The results are shown in FIG. 3. The same procedure is applied to the hPD-L1 tetramer.

In FIG. 3, (A) shows the mPD-L1 monomer binding to mPD-1/Fc, while (B) shows the mPD-L1 tetramer binding to mPD-1/Fc.
Results The Kd value (dissociation constant) of the mPD-L1 monomer was $8.6\times10^{-6}$, while that of the mPD-L1 tetramer was $5.9\times10^{-8}$ against mPD-1/Fc. The mPD-L1 tetramer exhibited increase in the binding activity by about 150 times the monomer (see FIGS. 3(A) and 3(B)).

The Kd value of the mPD-1 monomer was $5.6\times10^{-6}$, while that of the mPD-1 tetramer was $2.8\times10^{-8}$ against mPD-L1/Fc. The mPD-1 tetramer exhibited increase in the binding activity by about 200 times the monomer.

The Kd value of the hPD-1 monomer was $1.9\times10^{-6}$, while that of the hPD-1 tetramer was $7.3\times10^{-8}$ against hPD-L1/Fc. The hPD-1 tetramer exhibited increase in the binding activity by about 26 times the monomer.

Example 6

Binding Inhibition Analysis by Flow Cytometer

Binding inhibition by the mPD-L1 tetramer was carried out in accordance with the method described in the latter part of Example 4.

$5\times10^5$ of IIA. 6/mPD-1 cells were dyed with 10 μg/mL of mPD-L1/Fc and an FITC-labeled anti-Fc antibody in the presence or the absence of 100 μg/mL of the mPD-L1 tetramer. The results are shown in FIG. 4A. The same procedure is applied to the mPD-1 tetramer, using P815/hPD-L1 cells.

In the figure, the heavy line shows the case of the mPD-L1 tetramer free, the thin line shows the case added with the mPD-L1 tetramer, and the dotted line shows a control, i.e., the case added with a FITC conjugated secondary antibody.
Results The mPD-L1 tetramer inhibited mPD-L1/Fc binding to the IIA. 6/mPD-1 cells (see FIG. 4A).

Example 7

Measurement of Cell Growth-Promoting Activity $1\times10^5$ of lymphoid cells (spleen cells secondary lymph node cells) derived from 2C transgenic (Tg) mice (Journal of Immunology, 1996, Vol. 157, No. 2, pp. 670-678), together with mitomycin C-treated spleen cells derived from Balb/c mice were cultured at 37° C. for 3 days. Further, they were cultured in the presence of 3 and 10 μg/mL of an antimouse PD-1 antibody, an antimouse PD-L1 antibody and the mPD-L1 tetramer, respectively. 2 μCi of [$^3$H]-thymidine was added thereto 14 hours before the measurement, which were further cultured. The measurement of the cell-proliferating activity was measured in accordance with a known method. The results are shown in FIG. 4B. The same procedure is applied to the mPD-1 tetramer.

The numbers in the figure mean the followings, respectively;
1: Unstimulated group (background), 2: Phosphate buffer solution-added group (control), 3: 3 μg/mL of anti-mPD-1 antibody-added group, 4: 10 μg/mL of anti-mPD-1 antibody-added group, 5: 3 μg/mL of anti-mPD-L1 antibody-added group, 6: 10 μg/mL of anti-mPD-L1 antibody-added group, 7: 3 μg/ml, of mPD-L1 tetramer-added group, 8: 10 μg/mL of mPD-L1 tetramer-added group.

Results

The mPD-L1 tetramer exhibited remarkable cell-proliferating activity for lymphoid cells, compared to the anti-mouse PD-1 antibody and the anti-mouse PD-L1 antibody (see FIG. 4B, 7 and 8).

Example 8

Measurement of Cytotoxic Activity

Cytotoxic activity was measured in accordance with a method described in Example 1 of WO 2004/004771.

Lymphoid cells derived from the 2CTg mice were cultured at 37° C. for 2 weeks, together with mitomycin C-treated spleen cells derived from Ba1b/c mice. $1 \times 10^4$ to $8 \times 10^4$ of cells (effector cells), which were differentiated into CD8 positive T-cells by coculture, were cultured at 37° C. for S hours in the presence of 5 μg/mL of the antimouse PD-1 antibody, anti-mPD-L1 antibody and mPD-L1 tetramer, respectively, together with $1 \times 10^4$ of spleen cells (target cells) derived from the Ba1b/c mice, which were labeled with $^{51}$Cr-sodium citrate. Then, the cytotoxic activities of effector cells against the target cells were measured. The results are shown in FIG. 4C. The same procedure is applied to the mPD-1 tetramer.

White circles in the figure mean the control group, black triangles mean the mPD-L1 tetramer-added group, black squares mean the anti-mPD-1 antibody-added group, and black circles mean the anti-mPD-L1 antibody-added group. E/T ratio means a ratio of the effector (E) cell population to the target (T) cell population.

Results

The mPD-L1 tetramer enhanced the cytotoxic activity of the lymphoid cells on the same level as the anti-mPD-1 antibody or anti-mPD-L1 antibody (see black triangles in FIG. 4C).

Example 9

Analysis of Binding Specificity

Fc blocking antibody or R-RE was added to the anti-CD3 antibody-stimulated spleen cells isolated from PD-1-defect mice (see Non-Patent Document 3), to which 5 μg/mL of the mPD-L1 tetramer (conjugated with R-PE-streptoavidin) and mPD-1 antibody (conjugated with R—PE) were added, respectively. The analysis was performed in the same manner as in Example 4, using a flow cytometer.

Likewise, Fc blocking antibody or R-RE was added to LPS (lippolysaccharide)-stimulated spleen cells isolated from the PD-1-defect mice, to which 5 μg/mL of the ran-L1 tetramer and anti-mPD-1 antibody were added, respectively, and the analysis was performed in the same manner. The results are shown in FIG. 5. The same procedure is applied to the mPD-1 tetramer.

In the figure, (A) shows the bindings of the anti-mPD-1 antibody and mPD-L1 tetramer to the anti-CD3 antibody-stimulated spleen cells isolated from the PD-1-defect mice, and (B) shows the bindings of them to the LPS-stimulated spleen cells isolated from said mice in comparative manner. In each figure, the heavy line shows the case added with the mPD-L1 tetramer, the thin line shows the case added with the anti-mPD-1 antibody, and the dotted line shows the control. The arrow in the figure shows a shift in the histogram resulted from addition of the anti-mPD-1 antibody.

Results

Since the PD-1-defect mice do not express PD-1, the anti-mPD-1 antibody should not have been bound in principle. However, the antibody was somewhat bound to the LPS-stimulated spleen cells of the PD-1-defect mice (FIG. 5, thin line of B (arrow)). On the other hand, it was not observed at all that the mPD-L1 tetramer was bound to the spleen cells of the PD-1-defect mice (FIG. 5, heavy lines of A and B).

Formulation Examples

Formulation Example 1

A solution containing a multimer comprising the human PD-1 extracellular domain comprising the amino acid sequence of SEQ ID NO: 1 (1 g), mannitol (1 g) and Polysorbate 80 (10 mg) in 100 mL of physiological saline was prepared in an aseptic manner. The solution was dispensed into vials by 1 mL, freeze-dried and then sealed.

Formulation Example 2

A solution containing a multimer comprising the human PD-1 extracellular domain comprising the amino acid sequence of SEQ ID NO: 1 (1 g) and 100 mg of human serum albumin in 100 mL of a 0.02 M phosphate buffer solution (containing 0.15 M of sodium chloride and 0.01% Polysorbate 80 (pH 7.4)) was prepared in an aseptic manner, and dispensed into vials by 1 mL. Then, the solution in the each vial was freeze-dried and then sealed.

Formulation Example 3

A solution containing a multimer comprising the human PD-1 extracellular domain comprising the amino acid sequence of SEQ ID NO: 1 (1 g), sorbitol (2 mg), glycine (2 mg) and Polysorbate 80 (10 mg) in 100 mL of distilled water for injection was prepared in an aseptic manner, dispensed into vials by 1 mL, freeze-dried and then sealed.

Industrial Applicability

The multimer comprising the extracellular domain of PD-1, PD-L1 or PD-L2 is useful as a preventive and/or therapeutic drug for cancers, cancer metastasis, immune deficiency syndrome and infectious diseases. Also, the labeling agent of the multimer is used as an excellent test or diagnostic drug or a research reagent that is able to recognize and detect each ligand, specifically.

SEQUENCE LISTING

<160> NUMBER OF SEQ ID NOS: 18

Figure 1:
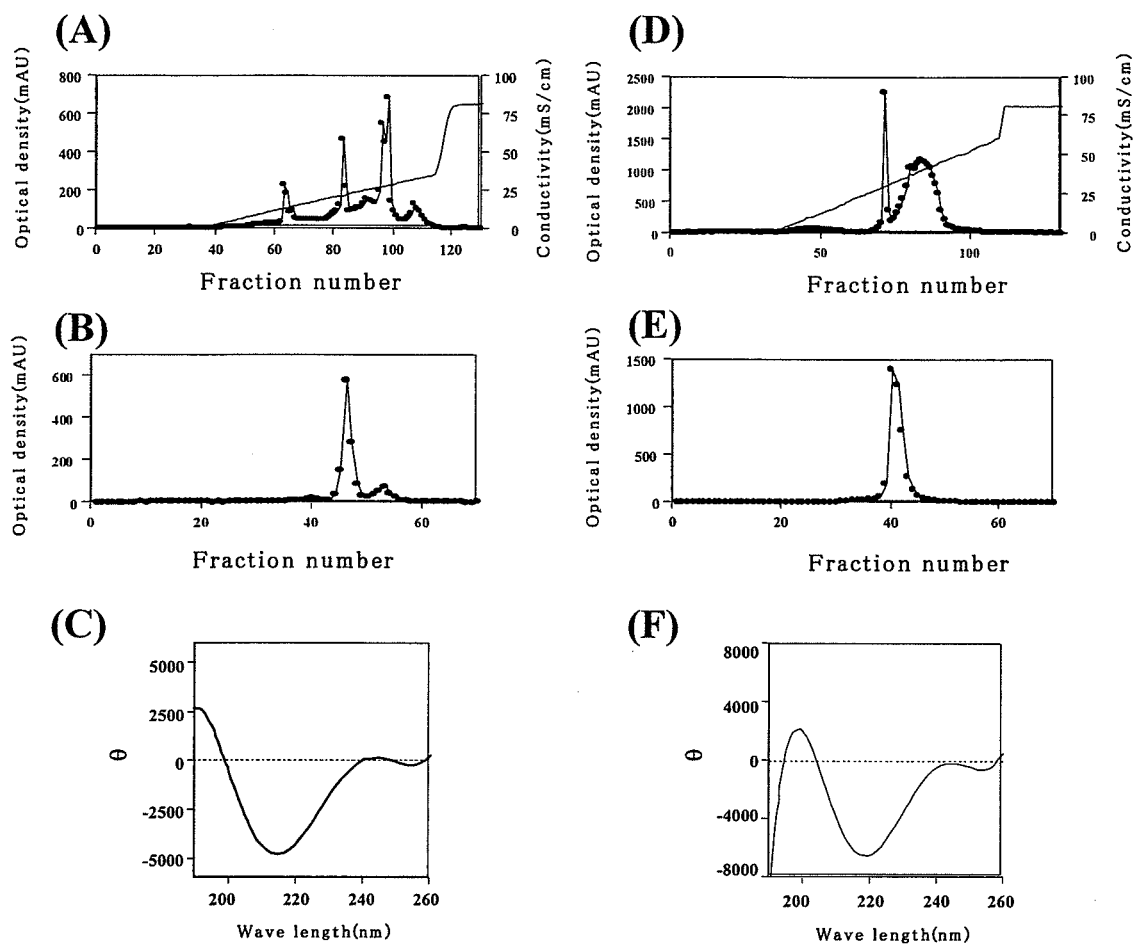
FIG. 1 shows preparation and analysis of the extracellular domains of PD-1 and PD-L1 in Example 2.
Figure 2:
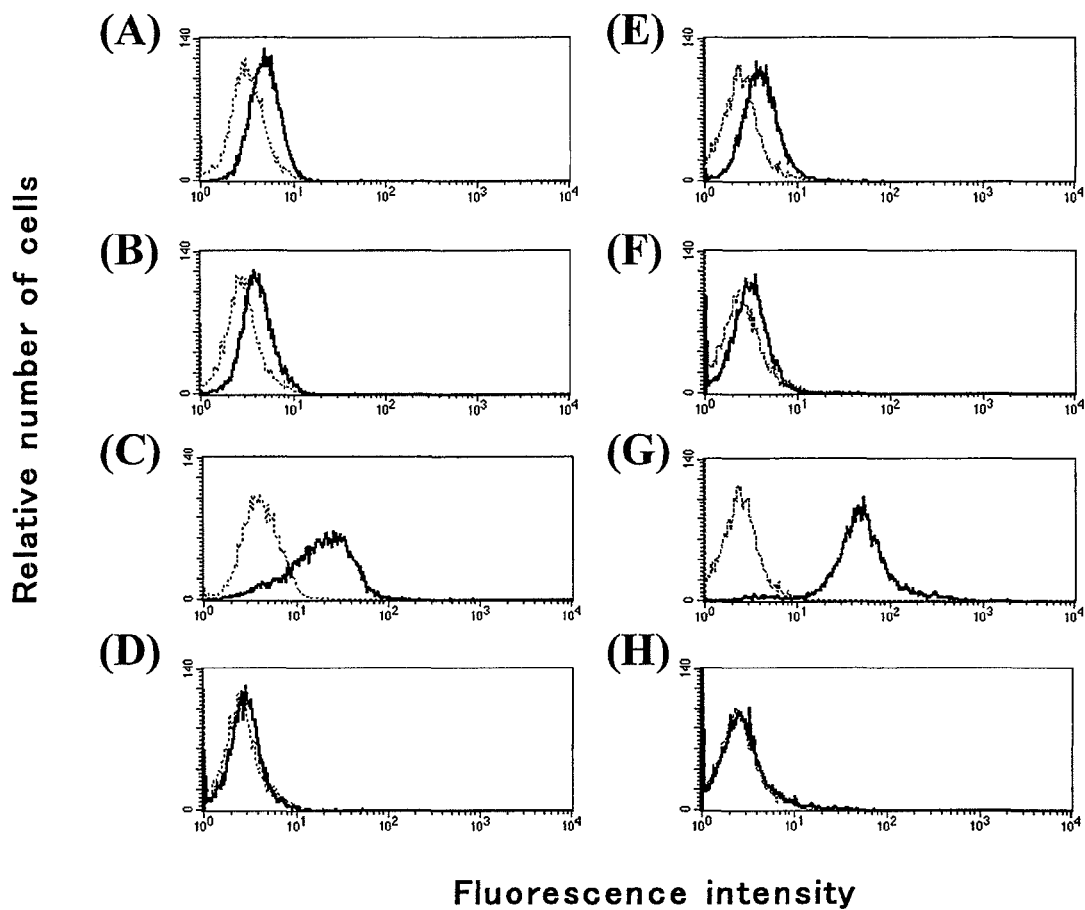
FIG. 2 shows the binding analysis of the PD-1 tetramer and the PD-L1 tetramer by flow cytometry in Example 4.
Figure 3:
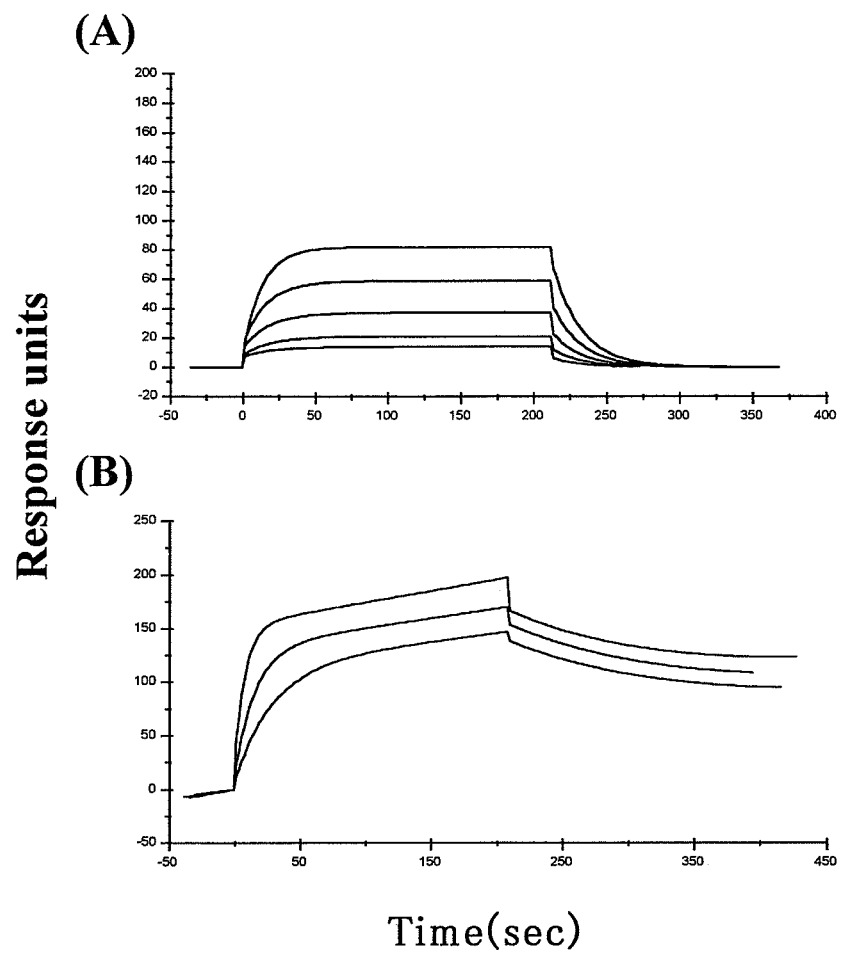
FIG. 3 shows the surface plasmon resonance analysis of the PD-L1 tetramer in Example 5.
Figure 4:
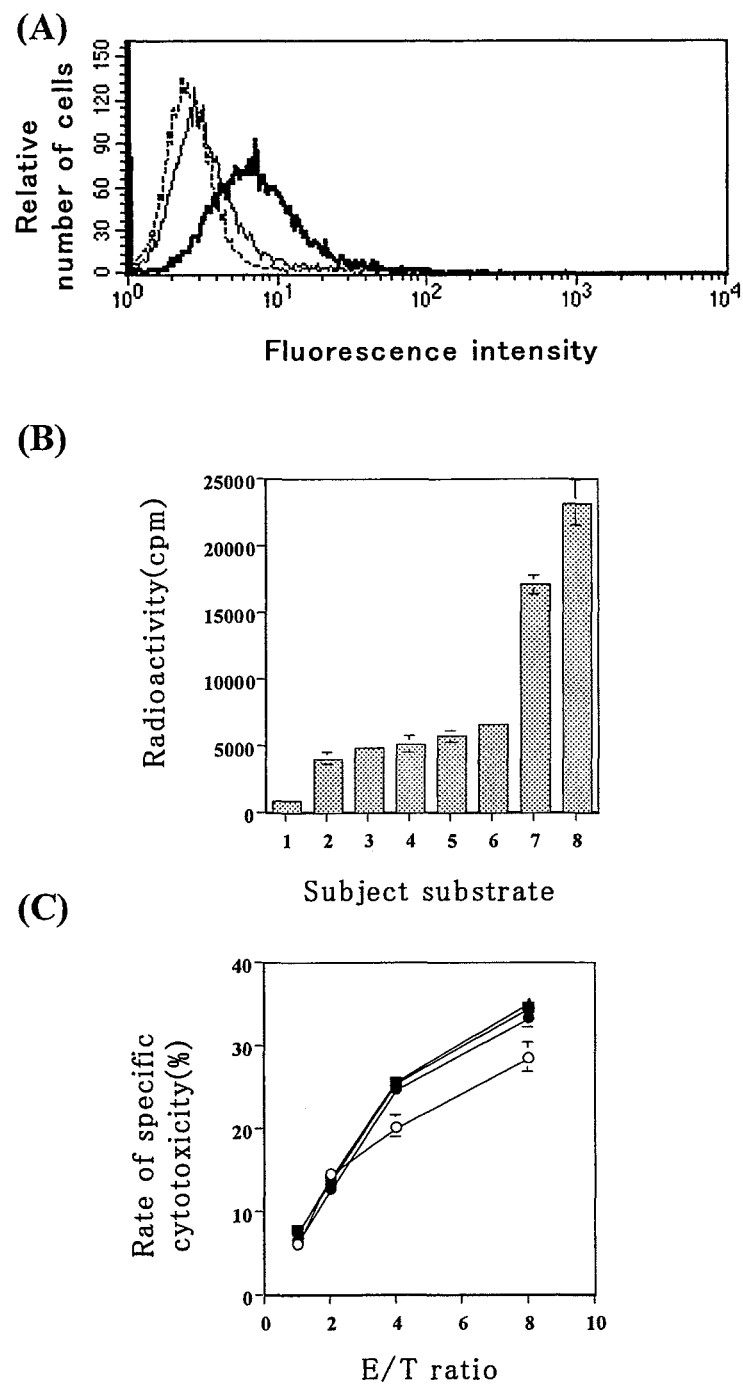
FIG. 4 shows the analysis of the cell binding inhibition, cell growth-promoting stimulus and cytotoxic activity-enhancing effect in Examples 6 to 8.
Figure 5:
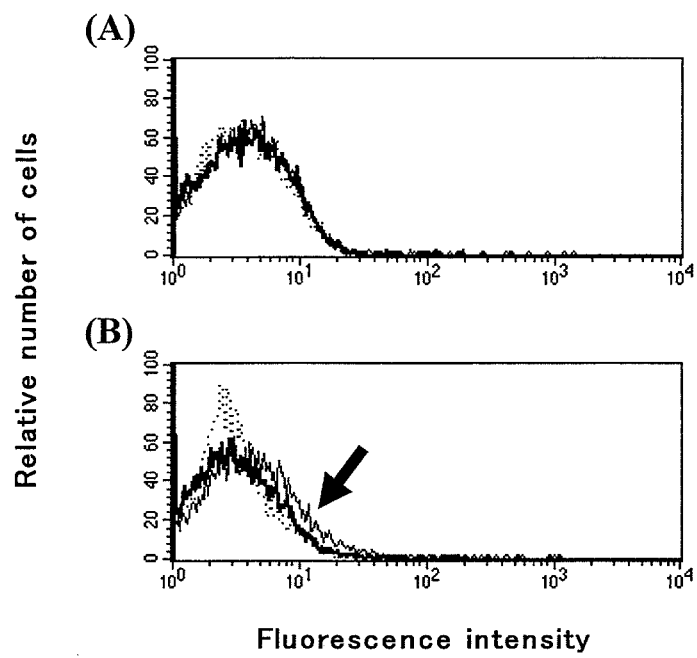
FIG. 5 shows the analysis of the binding specificity of the PD-L1 tetramer in Example 9.

<210> SEQ ID NO 1
<211> LENGTH: 504
<212> TYPE: PRT
<213> ORGANISM: Artificial sequence
<220> FEATURE:
<221> NAME/KEY: misc_feature
<222> LOCATION: (124)..(129)
<223> OTHER INFORMATION: Xaa stands for any amino acid
<220> FEATURE:
<221> NAME/KEY: misc_feature
<222> LOCATION: (251)..(256)
<223> OTHER INFORMATION: Xaa stands for any amino acid
<220> FEATURE:
<221> NAME/KEY: misc_feature
<222> LOCATION: (378)..(383)
<223> OTHER INFORMATION: Xaa stands for any amino acid
<220> FEATURE:
<223> OTHER INFORMATION: Synthetic construct (Tetramer of human PD-1)

<400> SEQUENCE: 1

```
Met Phe Leu Asp Ser Pro Asp Arg Pro Trp Asn Pro Pro Thr Phe Phe
 1               5                  10                  15

Pro Ala Leu Leu Val Val Thr Glu Gly Asp Asn Ala Thr Phe Thr Cys
            20                  25                  30

Ser Phe Ser Asn Thr Ser Glu Ser Phe Val Leu Asn Trp Tyr Arg Met
        35                  40                  45

Ser Pro Ser Asn Gln Thr Asp Lys Leu Ala Ala Phe Pro Glu Asp Arg
50                  55                  60

Ser Gln Pro Gly Gln Asp Ser Arg Phe Arg Val Thr Gln Leu Pro Asn
65                  70                  75                  80

Gly Arg Asp Phe His Met Ser Val Val Arg Ala Arg Arg Asn Asp Ser
                85                  90                  95

Gly Thr Tyr Leu Cys Gly Ala Ile Ser Leu Ala Pro Lys Ala Gln Ile
            100                 105                 110

Lys Glu Ser Leu Arg Ala Glu Leu Arg Val Thr Xaa Xaa Xaa Xaa Xaa
        115                 120                 125

Xaa Leu Asp Ser Pro Asp Arg Pro Trp Asn Pro Pro Thr Phe Phe Pro
    130                 135                 140

Ala Leu Leu Val Val Thr Glu Gly Asp Asn Ala Thr Phe Thr Cys Ser
145                 150                 155                 160

Phe Ser Asn Thr Ser Glu Ser Phe Val Leu Asn Trp Tyr Arg Met Ser
                165                 170                 175

Pro Ser Asn Gln Thr Asp Lys Leu Ala Ala Phe Pro Glu Asp Arg Ser
            180                 185                 190

Gln Pro Gly Gln Asp Ser Arg Phe Arg Val Thr Gln Leu Pro Asn Gly
        195                 200                 205

Arg Asp Phe His Met Ser Val Val Arg Ala Arg Arg Asn Asp Ser Gly
    210                 215                 220

Thr Tyr Leu Cys Gly Ala Ile Ser Leu Ala Pro Lys Ala Gln Ile Lys
225                 230                 235                 240

Glu Ser Leu Arg Ala Glu Leu Arg Val Thr Xaa Xaa Xaa Xaa Xaa Xaa
                245                 250                 255

Leu Asp Ser Pro Asp Arg Pro Trp Asn Pro Pro Thr Phe Phe Pro Ala
            260                 265                 270

Leu Leu Val Val Thr Glu Gly Asp Asn Ala Thr Phe Thr Cys Ser Phe
        275                 280                 285
```

```
Ser Asn Thr Ser Glu Ser Phe Val Leu Asn Trp Tyr Arg Met Ser Pro
            290                 295                 300

Ser Asn Gln Thr Asp Lys Leu Ala Ala Phe Pro Glu Asp Arg Ser Gln
305                 310                 315                 320

Pro Gly Gln Asp Ser Arg Phe Arg Val Thr Gln Leu Pro Asn Gly Arg
                325                 330                 335

Asp Phe His Met Ser Val Val Arg Ala Arg Arg Asn Asp Ser Gly Thr
                    340                 345                 350

Tyr Leu Cys Gly Ala Ile Ser Leu Ala Pro Lys Ala Gln Ile Lys Glu
            355                 360                 365

Ser Leu Arg Ala Glu Leu Arg Val Thr Xaa Xaa Xaa Xaa Xaa Xaa Leu
370                 375                 380

Asp Ser Pro Asp Arg Pro Trp Asn Pro Pro Thr Phe Phe Pro Ala Leu
385                 390                 395                 400

Leu Val Val Thr Glu Gly Asp Asn Ala Thr Phe Thr Cys Ser Phe Ser
                405                 410                 415

Asn Thr Ser Glu Ser Phe Val Leu Asn Trp Tyr Arg Met Ser Pro Ser
                    420                 425                 430

Asn Gln Thr Asp Lys Leu Ala Ala Phe Pro Glu Asp Arg Ser Gln Pro
            435                 440                 445

Gly Gln Asp Ser Arg Phe Arg Val Thr Gln Leu Pro Asn Gly Arg Asp
450                 455                 460

Phe His Met Ser Val Val Arg Ala Arg Arg Asn Asp Ser Gly Thr Tyr
465                 470                 475                 480

Leu Cys Gly Ala Ile Ser Leu Ala Pro Lys Ala Gln Ile Lys Glu Ser
                485                 490                 495

Leu Arg Ala Glu Leu Arg Val Thr
            500
```

<210> SEQ ID NO 2
<211> LENGTH: 1515
<212> TYPE: DNA
<213> ORGANISM: Artificial sequence
<220> FEATURE:
<221> NAME/KEY: misc_feature
<222> LOCATION: (370)..(387)
<223> OTHER INFORMATION: n stands for any base
<220> FEATURE:
<221> NAME/KEY: misc_feature
<222> LOCATION: (751)..(768)
<223> OTHER INFORMATION: n stands for any base
<220> FEATURE:
<221> NAME/KEY: misc_feature
<222> LOCATION: (1132)..(1149)
<223> OTHER INFORMATION: n stands for any base
<220> FEATURE:
<223> OTHER INFORMATION: Synthetic construct (Tetramer of human PD-1)

<400> SEQUENCE: 2

```
atgttcttag actccccaga caggccctgg aaccccccca ccttcttccc agccctgctc    60
gtggtgaccg aaggggacaa cgccaccttc acctgcagct ctccaacac atcggagagc    120 ttcgtgctaa actggtaccg catgagcccc agcaaccaga cggacaagct ggccgccttc    180
cccgaggacc gcagccagcc cggccaggac tcccgcttcc gtgtcacaca actgcccaac    240
gggcgtgact ccacatgag cgtggtcagg gccggcgca atgacagcgg cacctacctc    300
tgtggggcca tctccctggc ccccaaggcg cagatcaaag agagcctgcg ggcagagctc    360
agggtgacan nnnnnnnnn nnnnnnntta gactccccag acaggccctg gaaccccccca    420 accttcttcc cagccctgct cgtggtgacc gaaggggaca cgccaccttt cacctgcagc    480
```

-continued

```
ttctccaaca catcggagag cttcgtgcta aactggtacc gcatgagccc cagcaaccag    540
acggacaagc tggccgcctt ccccgaggac cgcagccagc ccggccagga ctcccgcttc    600
cgtgtcacac aactgcccaa cgggcgtgac ttccacatga gcgtggtcag ggcccggcgc    660
aatgacagcg gcacctacct ctgtggggcc atctccctgg cccccaaggc gcagatcaaa    720
gagagcctgc gggcagagct cagggtgaca nnnnnnnnnn nnnnnnnntt agactcccca    780
gacaggccct ggaacccccc caccttcttc ccagccctgc tcgtggtgac cgaaggggac    840
aacgccacct tcacctgcag cttctccaac acatcggaga gcttcgtgct aaactggtac    900
cgcatgagcc ccagcaacca gacggacaag ctggccgcct tccccgagga ccgcagccag    960
cccggccagg actcccgctt ccgtgtcaca caactgccca cgggcgtga cttccacatg    1020 agcgtggtca gggcccggcg caatgacagc ggcacctacc tctgtggggc catctccctg    1080
gcccccaagg cgcagatcaa agagagcctg cgggcagagc tcagggtgac annnnnnnnn    1140
nnnnnnnnnt tagactcccc agacaggccc tggaaccccc ccaccttctt cccagccctg    1200
ctcgtggtga ccgaagggga caacgccacc ttcacctgca gcttctccaa cacatcggag    1260
agcttcgtgc taaactggta ccgcatgagc cccagcaacc agacggacaa gctggccgcc    1320
ttccccgagg accgcagcca gcccggccag gactcccgct tccgtgtcac acaactgccc    1380
aacgggcgtg acttccacat gagcgtggtc agggcccggc gcaatgacag cggcacctac    1440
ctctgtgggg ccatctccct ggcccccaag gcgcagatca agagagcct gcgggcagag    1500 ctcagggtga cataa                                                    1515
```

<210> SEQ ID NO 3
<211> LENGTH: 504
<212> TYPE: PRT
<213> ORGANISM: Artificial sequence
<220> FEATURE:
<221> NAME/KEY: misc_feature
<222> LOCATION: (124)..(129)
<223> OTHER INFORMATION: Xaa stands for any amino acid
<220> FEATURE:
<221> NAME/KEY: misc_feature
<222> LOCATION: (251)..(256)
<223> OTHER INFORMATION: Xaa stands for any amino acid
<220> FEATURE:
<221> NAME/KEY: misc_feature
<222> LOCATION: (378)..(383)
<223> OTHER INFORMATION: Xaa stands for any amino acid
<220> FEATURE:
<223> OTHER INFORMATION: Synthetic construct (Tetramer of mouse PD-1)

<400> SEQUENCE: 3

```
Met Ala Leu Glu Val Pro Asn Gly Pro Trp Arg Ser Leu Thr Phe Tyr
1               5                   10                  15

Pro Ala Trp Leu Thr Val Ser Glu Gly Ala Asn Ala Thr Phe Thr Cys
            20                  25                  30

Ser Leu Ser Asn Trp Ser Glu Asp Leu Met Leu Asn Trp Asn Arg Leu
        35                  40                  45

Ser Pro Ser Asn Gln Thr Glu Lys Gln Ala Ala Phe Ser Asn Gly Leu
    50                  55                  60

Ser Gln Pro Val Gln Asp Ala Arg Phe Gln Ile Ile Gln Leu Pro Asn
65                  70                  75                  80

Arg His Asp Phe His Met Asn Ile Leu Asp Thr Arg Arg Asn Asp Ser
                85                  90                  95

Gly Ile Tyr Leu Cys Gly Ala Ile Ser Leu His Pro Lys Ala Lys Ile
            100                 105                 110

Glu Glu Ser Pro Gly Ala Glu Leu Val Val Thr Xaa Xaa Xaa Xaa Xaa
```

```
            115                 120                 125
Xaa Leu Glu Val Pro Asn Gly Pro Trp Arg Ser Leu Thr Phe Tyr Pro
130                 135                 140

Ala Trp Leu Thr Val Ser Glu Gly Ala Asn Ala Thr Phe Thr Cys Ser
145                 150                 155                 160

Leu Ser Asn Trp Ser Glu Asp Leu Met Leu Asn Trp Asn Arg Leu Ser
                165                 170                 175

Pro Ser Asn Gln Thr Glu Lys Gln Ala Ala Phe Ser Asn Gly Leu Ser
                180                 185                 190

Gln Pro Val Gln Asp Ala Arg Phe Gln Ile Ile Gln Leu Pro Asn Arg
            195                 200                 205

His Asp Phe His Met Asn Ile Leu Asp Thr Arg Arg Asn Asp Ser Gly
210                 215                 220

Ile Tyr Leu Cys Gly Ala Ile Ser Leu His Pro Lys Ala Lys Ile Glu
225                 230                 235                 240

Glu Ser Pro Gly Ala Glu Leu Val Val Thr Xaa Xaa Xaa Xaa Xaa Xaa
                245                 250                 255

Leu Glu Val Pro Asn Gly Pro Trp Arg Ser Leu Thr Phe Tyr Pro Ala
            260                 265                 270

Trp Leu Thr Val Ser Glu Gly Ala Asn Ala Thr Phe Thr Cys Ser Leu
            275                 280                 285

Ser Asn Trp Ser Glu Asp Leu Met Leu Asn Trp Asn Arg Leu Ser Pro
290                 295                 300

Ser Asn Gln Thr Glu Lys Gln Ala Ala Phe Ser Asn Gly Leu Ser Gln
305                 310                 315                 320

Pro Val Gln Asp Ala Arg Phe Gln Ile Ile Gln Leu Pro Asn Arg His
                325                 330                 335

Asp Phe His Met Asn Ile Leu Asp Thr Arg Arg Asn Asp Ser Gly Ile
                340                 345                 350

Tyr Leu Cys Gly Ala Ile Ser Leu His Pro Lys Ala Lys Ile Glu Glu
            355                 360                 365

Ser Pro Gly Ala Glu Leu Val Val Thr Xaa Xaa Xaa Xaa Xaa Xaa Leu
370                 375                 380

Glu Val Pro Asn Gly Pro Trp Arg Ser Leu Thr Phe Tyr Pro Ala Trp
385                 390                 395                 400

Leu Thr Val Ser Glu Gly Ala Asn Ala Thr Phe Thr Cys Ser Leu Ser
                405                 410                 415

Asn Trp Ser Glu Asp Leu Met Leu Asn Trp Asn Arg Leu Ser Pro Ser
                420                 425                 430

Asn Gln Thr Glu Lys Gln Ala Ala Phe Ser Asn Gly Leu Ser Gln Pro
            435                 440                 445

Val Gln Asp Ala Arg Phe Gln Ile Ile Gln Leu Pro Asn Arg His Asp
450                 455                 460

Phe His Met Asn Ile Leu Asp Thr Arg Arg Asn Asp Ser Gly Ile Tyr
465                 470                 475                 480

Leu Cys Gly Ala Ile Ser Leu His Pro Lys Ala Lys Ile Glu Glu Ser
                485                 490                 495

Pro Gly Ala Glu Leu Val Val Thr
            500

<210> SEQ ID NO 4
<211> LENGTH: 1515
<212> TYPE: DNA
<213> ORGANISM: Artificial sequence
<220> FEATURE:
```

```
<221> NAME/KEY: misc_feature
<222> LOCATION: (370)..(387)
<223> OTHER INFORMATION: n stands for any base
<220> FEATURE:
<221> NAME/KEY: misc_feature
<222> LOCATION: (751)..(768)
<223> OTHER INFORMATION: n stands for any base
<220> FEATURE:
<221> NAME/KEY: misc_feature
<222> LOCATION: (1132)..(1149)
<223> OTHER INFORMATION: n stands for any base
<220> FEATURE:
<223> OTHER INFORMATION: Synthetic construct (Tetramer of mouse PD-1)

<400> SEQUENCE: 4
atggcactag aggtccccaa tgggccctgg aggtccctca ccttctaccc agcctggctc      60
acagtgtcag agggagcaaa tgccaccttc acctgcagct gtccaactg gtcggaggat     120 cttatgctga actggaaccg cctgagtccc agcaaccaga ctgaaaaaca ggccgccttc    180
tctaatggtt tgagccaacc cgtccaggat gcccgcttcc agatcataca gctgcccaac    240
aggcatgact tccacatgaa catccttgac acacggcgca atgacagtgg catctacctc    300
tgtggggcca tctccctgca ccccaaggca aaaatcgagg agagccctgg agcagagctc    360
gtggtaacan nnnnnnnnn nnnnnnncta gaggtcccca atgggccctg gaggtccctc    420
accttctacc cagcctggct cacagtgtca gagggagcaa atgccacctt cacctgcagc    480
ttgtccaact ggtcggagga tcttatgctg aactggaacc gcctgagtcc cagcaaccag    540
actgaaaaac aggccgcctt ctctaatggt ttgagccaac ccgtccagga tgcccgcttc    600
cagatcatac agctgcccaa caggcatgac ttccacatga acatccttga cacacggcgc    660
aatgacagtg gcatctacct ctgtggggcc atctccctgc accccaaggc aaaaatcgag    720
gagagccctg gagcagagct cgtggtaaca nnnnnnnnnn nnnnnnnnct agaggtcccc    780
aatgggccct ggaggtccct caccttctac ccagcctggc tcacagtgtc agagggagca    840
aatgccacct tcacctgcag cttgtccaac tggtcggagg atcttatgct gaactggaac    900
cgcctgagtc ccagcaacca gactgaaaaa caggccgcct tctctaatgg tttgagccaa    960
cccgtccagg atgcccgctt ccagatcata cagctgccca acaggcatga cttccacatg   1020
aacatccttg acacacggcg caatgacagt ggcatctacc tctgtggggc catctccctg   1080
caccccaagg caaaaatcga ggagagccct ggagcagagc tcgtggtaac annnnnnnnn   1140
nnnnnnnnnc tagaggtccc caatgggccc tggaggtccc tcaccttcta cccagcctgg   1200
ctcacagtgt cagagggagc aaatgccacc ttcacctgca gcttgtccaa ctggtcggag   1260
gatcttatgc tgaactggaa ccgcctgagt cccagcaacc agactgaaaa acaggccgcc   1320
ttctctaatg gtttgagcca acccgtccag gatgcccgct tccagatcat acagctgccc   1380
aacaggcatg acttccacat gaacatcctt gacacacggc gcaatgacag tggcatctac   1440
ctctgtgggg ccatctccct gcaccccaag gcaaaaatcg aggagagccc tggagcagag   1500
ctcgtggtaa cataa                                                    1515

<210> SEQ ID NO 5
<211> LENGTH: 871
<212> TYPE: PRT
<213> ORGANISM: Artificial sequence
<220> FEATURE:
<221> NAME/KEY: misc_feature
<222> LOCATION: (215)..(220)
<223> OTHER INFORMATION: Xaa stands for any amino acid
<220> FEATURE:
<221> NAME/KEY: misc_feature
<222> LOCATION: (434)..(439)
```

```
<223> OTHER INFORMATION: Xaa stands for any amino acid
<220> FEATURE:
<221> NAME/KEY: misc_feature
<222> LOCATION: (653)..(658)
<223> OTHER INFORMATION: Xaa stands for any amino acid
<220> FEATURE:
<223> OTHER INFORMATION: Synthetic construct (Tetramer of human PD-L1)

<400> SEQUENCE: 5

Met Ala Phe Thr Val Thr Val Pro Lys Asp Leu Tyr Val Val Glu Tyr
1               5                   10                  15

Gly Ser Asn Met Thr Ile Glu Cys Lys Phe Pro Val Glu Lys Gln Leu
            20                  25                  30

Asp Leu Ala Ala Leu Ile Val Tyr Trp Glu Met Glu Asp Lys Asn Ile
        35                  40                  45

Ile Gln Phe Val His Gly Glu Glu Asp Leu Lys Val Gln His Ser Ser
    50                  55                  60

Tyr Arg Gln Arg Ala Arg Leu Leu Lys Asp Gln Leu Ser Leu Gly Asn
65                  70                  75                  80

Ala Ala Leu Gln Ile Thr Asp Val Lys Leu Gln Asp Ala Gly Val Tyr
                85                  90                  95

Arg Cys Met Ile Ser Tyr Gly Gly Ala Asp Tyr Lys Arg Ile Thr Val
            100                 105                 110

Lys Val Asn Ala Pro Tyr Asn Lys Ile Asn Gln Arg Ile Leu Val Val
        115                 120                 125

Asp Pro Val Thr Ser Glu His Glu Leu Thr Cys Gln Ala Glu Gly Tyr
    130                 135                 140

Pro Lys Ala Glu Val Ile Trp Thr Ser Ser Asp His Gln Val Leu Ser
145                 150                 155                 160

Gly Lys Thr Thr Thr Thr Asn Ser Lys Arg Glu Glu Lys Leu Phe Asn
                165                 170                 175

Val Thr Ser Thr Leu Arg Ile Asn Thr Thr Thr Asn Glu Ile Phe Tyr
            180                 185                 190

Cys Thr Phe Arg Arg Leu Asp Pro Glu Glu Asn His Thr Ala Glu Leu
        195                 200                 205

Val Ile Pro Glu Leu Pro Xaa Xaa Xaa Xaa Xaa Xaa Ala Phe Thr Val
    210                 215                 220

Thr Val Pro Lys Asp Leu Tyr Val Val Glu Tyr Gly Ser Asn Met Thr
225                 230                 235                 240

Ile Glu Cys Lys Phe Pro Val Glu Lys Gln Leu Asp Leu Ala Ala Leu
                245                 250                 255

Ile Val Tyr Trp Glu Met Glu Asp Lys Asn Ile Ile Gln Phe Val His
            260                 265                 270

Gly Glu Glu Asp Leu Lys Val Gln His Ser Ser Tyr Arg Gln Arg Ala
        275                 280                 285

Arg Leu Leu Lys Asp Gln Leu Ser Leu Gly Asn Ala Ala Leu Gln Ile
    290                 295                 300

Thr Asp Val Lys Leu Gln Asp Ala Gly Val Tyr Arg Cys Met Ile Ser
305                 310                 315                 320

Tyr Gly Gly Ala Asp Tyr Lys Arg Ile Thr Val Lys Val Asn Ala Pro
                325                 330                 335

Tyr Asn Lys Ile Asn Gln Arg Ile Leu Val Val Asp Pro Val Thr Ser
            340                 345                 350

Glu His Glu Leu Thr Cys Gln Ala Glu Gly Tyr Pro Lys Ala Glu Val
        355                 360                 365

Ile Trp Thr Ser Ser Asp His Gln Val Leu Ser Gly Lys Thr Thr Thr
```

```
              370                 375                 380
Thr Asn Ser Lys Arg Glu Glu Lys Leu Phe Asn Val Thr Ser Thr Leu
385                 390                 395                 400

Arg Ile Asn Thr Thr Thr Asn Glu Ile Phe Tyr Cys Thr Phe Arg Arg
                    405                 410                 415

Leu Asp Pro Glu Glu Asn His Thr Ala Glu Leu Val Ile Pro Glu Leu
                420                 425                 430

Pro Xaa Xaa Xaa Xaa Xaa Ala Phe Thr Val Thr Val Pro Lys Asp
            435                 440                 445

Leu Tyr Val Val Glu Tyr Gly Ser Asn Met Thr Ile Glu Cys Lys Phe
450                 455                 460

Pro Val Glu Lys Gln Leu Asp Leu Ala Ala Leu Ile Val Tyr Trp Glu
465                 470                 475                 480

Met Glu Asp Lys Asn Ile Ile Gln Phe Val His Gly Glu Glu Asp Leu
                485                 490                 495

Lys Val Gln His Ser Ser Tyr Arg Gln Arg Ala Arg Leu Leu Lys Asp
                500                 505                 510

Gln Leu Ser Leu Gly Asn Ala Ala Leu Gln Ile Thr Asp Val Lys Leu
            515                 520                 525

Gln Asp Ala Gly Val Tyr Arg Cys Met Ile Ser Tyr Gly Gly Ala Asp
530                 535                 540

Tyr Lys Arg Ile Thr Val Lys Val Asn Ala Pro Tyr Asn Lys Ile Asn
545                 550                 555                 560

Gln Arg Ile Leu Val Val Asp Pro Val Thr Ser Glu His Glu Leu Thr
                565                 570                 575

Cys Gln Ala Glu Gly Tyr Pro Lys Ala Glu Val Ile Trp Thr Ser Ser
                580                 585                 590

Asp His Gln Val Leu Ser Gly Lys Thr Thr Thr Thr Asn Ser Lys Arg
            595                 600                 605

Glu Glu Lys Leu Phe Asn Val Thr Ser Thr Leu Arg Ile Asn Thr Thr
610                 615                 620

Thr Asn Glu Ile Phe Tyr Cys Thr Phe Arg Arg Leu Asp Pro Glu Glu
625                 630                 635                 640

Asn His Thr Ala Glu Leu Val Ile Pro Glu Leu Pro Xaa Xaa Xaa Xaa
                645                 650                 655

Xaa Xaa Ala Phe Thr Val Thr Val Pro Lys Asp Leu Tyr Val Val Glu
            660                 665                 670

Tyr Gly Ser Asn Met Thr Ile Glu Cys Lys Phe Pro Val Glu Lys Gln
            675                 680                 685

Leu Asp Leu Ala Ala Leu Ile Val Tyr Trp Glu Met Glu Asp Lys Asn
            690                 695                 700

Ile Ile Gln Phe Val His Gly Glu Glu Asp Leu Lys Val Gln His Ser
705                 710                 715                 720

Ser Tyr Arg Gln Arg Ala Arg Leu Leu Lys Asp Gln Leu Ser Leu Gly
                725                 730                 735

Asn Ala Ala Leu Gln Ile Thr Asp Val Lys Leu Gln Asp Ala Gly Val
            740                 745                 750

Tyr Arg Cys Met Ile Ser Tyr Gly Gly Ala Asp Tyr Lys Arg Ile Thr
            755                 760                 765

Val Lys Val Asn Ala Pro Tyr Asn Lys Ile Asn Gln Arg Ile Leu Val
            770                 775                 780

Val Asp Pro Val Thr Ser Glu His Glu Leu Thr Cys Gln Ala Glu Gly
785                 790                 795                 800
```

-continued

```
Tyr Pro Lys Ala Glu Val Ile Trp Thr Ser Ser Asp His Gln Val Leu
            805                 810                 815

Ser Gly Lys Thr Thr Thr Asn Ser Lys Arg Glu Glu Lys Leu Phe
        820                 825                 830

Asn Val Thr Ser Thr Leu Arg Ile Asn Thr Thr Thr Asn Glu Ile Phe
            835                 840                 845

Tyr Cys Thr Phe Arg Arg Leu Asp Pro Glu Glu Asn His Thr Ala Glu
    850                 855                 860

Leu Val Ile Pro Glu Leu Pro
865                 870

<210> SEQ ID NO 6
<211> LENGTH: 2616
<212> TYPE: DNA
<213> ORGANISM: Artificial sequence
<220> FEATURE:
<221> NAME/KEY: misc_feature
<222> LOCATION: (643)..(660)
<223> OTHER INFORMATION: n stands for any base
<220> FEATURE:
<221> NAME/KEY: misc_feature
<222> LOCATION: (1300)..(1317)
<223> OTHER INFORMATION: n stands for any base
<220> FEATURE:
<221> NAME/KEY: misc_feature
<222> LOCATION: (1957)..(1974)
<223> OTHER INFORMATION: n stands for any base
<220> FEATURE:
<223> OTHER INFORMATION: Synthetic construct (Tetramer of human PD-L1)

<400> SEQUENCE: 6
atggcattta ctgtcacggt tcccaaggac ctatatgtgg tagagtatgg tagcaatatg      60
acaattgaat gcaaattccc agtagaaaaa caattagacc tggctgcact aattgtctat     120
tgggaaatgg aggataagaa cattattcaa tttgtgcatg agaggaaga cctgaaggtt     180 cagcatagta gctacagaca gagggcccgg ctgttgaagg accagctctc cctgggaaat     240
gctgcacttc agatcacaga tgtgaaattg caggatgcag gggtgtaccg ctgcatgatc     300
agctatggtg gtgccgacta caagcgaatt actgtgaaag tcaatgcccc atacaacaaa     360
atcaaccaaa gaattttggt tgtggatcca gtcacctctg aacatgaact gacatgtcag     420
gctgagggct accccaaggc cgaagtcatc tggacaagca gtgaccatca agtcctgagt     480
ggtaagacca ccaccaccaa ttccaagaga gaggagaagc ttttcaatgt gaccagcaca     540
ctgagaatca cacaacaac taatgagatt ttctactgca ctttttaggag attagatcct     600 gaggaaaacc atacagctga attggtcatc ccagaactac ctnnnnnnnn nnnnnnnnnn     660
gcatttactg tcacggttcc caaggaccta tatgtggtag agtatggtag caatatgaca     720
attgaatgca aattcccagt agaaaaacaa ttagacctgg ctgcactaat tgtctattgg     780
gaaatggagg ataagaacat tattcaattt gtgcatggag aggaagacct gaaggttcag     840
catagtagct acagacagag ggcccggctg ttgaaggacc agctctccct gggaaatgct     900
gcacttcaga tcacagatgt gaaattgcag gatgcagggg tgtaccgctg catgatcagc     960
tatggtggtg ccgactacaa gcgaattact gtgaaagtca atgccccata acaaaaatc    1020 aaccaaagaa ttttggttgt ggatccagtc acctctgaac atgaactgac atgtcaggct    1080
gagggctacc ccaaggccga agtcatctgg acaagcagtg accatcaagt cctgagtggt    1140
aagaccacca ccaccaattc aagagagag gagaagcttt tcaatgtgac cagcacactg    1200
agaatcaaca caacaactaa tgagattttc tactgcactt ttaggagatt agatcctgag    1260
gaaaaccata cagctgaatt ggtcatccca gaactacctn nnnnnnnnn nnnnnngca    1320
```

```
tttactgtca cggttcccaa ggacctatat gtggtagagt atggtagcaa tatgacaatt    1380
gaatgcaaat tcccagtaga aaacaatta gacctggctg cactaattgt ctattgggaa    1440
atggaggata agaacattat tcaatttgtg catggagagg aagacctgaa ggttcagcat    1500
agtagctaca gacagagggc ccggctgttg aaggaccagc tctccctggg aaatgctgca    1560
cttcagatca cagatgtgaa attgcaggat gcagggtgt accgctgcat gatcagctat     1620
ggtggtgccg actacaagcg aattactgtg aaagtcaatg ccccatacaa caaaatcaac    1680
caaagaattt tggttgtgga tccagtcacc tctgaacatg aactgacatg tcaggctgag    1740
ggctacccca aggccgaagt catctggaca agcagtgacc atcaagtcct gagtggtaag    1800
accaccacca ccaattccaa gagagaggag aagcttttca atgtgaccag cacactgaga    1860
atcaacacaa caactaatga atttcttctac tgcacttttta ggagattaga tcctgaggaa   1920
aaccatacag ctgaattggt catcccagaa ctacctnnnn nnnnnnnnn nnnngcattt     1980 actgtcacgg ttcccaagga cctatatgtg gtagagtatg gtagcaatat gacaattgaa    2040
tgcaaattcc cagtagaaaa acaattagac ctggctgcac taattgtcta ttgggaaatg    2100
gaggataaga acattattca atttgtgcat ggagaggaag acctgaaggt tcagcatagt    2160
agctacagac agagggcccg gctgttgaag gaccagctct ccctgggaaa tgctgcactt    2220
cagatcacag atgtgaaatt gcaggatgca ggggtgtacc gctgcatgat cagctatggt    2280
ggtgccgact acaagcgaat tactgtgaaa gtcaatgccc catacaacaa aatcaaccaa    2340
agaattttgg ttgtggatcc agtcacctct gaacatgaac tgacatgtca ggctgagggc    2400
taccccaagg ccgaagtcat ctggacaagc agtgaccatc aagtcctgag tggtaagacc    2460
accaccacca attccaagag agaggagaag cttttcaatg tgaccagcac actgagaatc    2520
aacacaacaa ctaatgagat tttctactgc acttttagga gattagatcc tgaggaaaac    2580
catacagctg aattggtcat cccagaacta ccttaa                             2616

<210> SEQ ID NO 7
<211> LENGTH: 867
<212> TYPE: PRT
<213> ORGANISM: Artificial sequence
<220> FEATURE:
<221> NAME/KEY: misc_feature
<222> LOCATION: (214)..(219)
<223> OTHER INFORMATION: Xaa stands for any amino acid
<220> FEATURE:
<221> NAME/KEY: misc_feature
<222> LOCATION: (432)..(437)
<223> OTHER INFORMATION: Xaa stands for any amino acid
<220> FEATURE:
<221> NAME/KEY: misc_feature
<222> LOCATION: (650)..(655)
<223> OTHER INFORMATION: Xaa stands for any amino acid
<220> FEATURE:
<223> OTHER INFORMATION: Synthetic construct (Tetramer of mouse PD-L1)

<400> SEQUENCE: 7

Met Ala Phe Thr Ile Thr Ala Pro Lys Asp Leu Tyr Val Val Glu Tyr
1               5                   10                  15

Gly Ser Asn Val Thr Met Glu Cys Arg Phe Pro Val Glu Arg Glu Leu
            20                  25                  30

Asp Leu Leu Ala Leu Val Val Tyr Trp Glu Lys Glu Asp Glu Gln Val
        35                  40                  45

Ile Gln Phe Val Ala Gly Glu Glu Asp Leu Lys Pro Gln His Ser Asn
    50                  55                  60

Phe Arg Gly Arg Ala Ser Leu Pro Lys Asp Gln Leu Leu Lys Gly Asn
```

```
              65                  70                  75                  80
Ala Ala Leu Gln Ile Thr Asp Val Lys Leu Gln Asp Ala Gly Val Tyr
                        85                  90                  95
Ser Cys Ile Ile Ser Tyr Gly Gly Ala Asp Tyr Lys Arg Ile Thr Leu
                    100                 105                 110
Lys Val Asn Ala Pro Tyr Arg Lys Ile Asn Gln Arg Ile Ser Val Asp
                115                 120                 125
Pro Ala Thr Ser Glu His Glu Leu Ile Cys Gln Ala Glu Gly Tyr Pro
            130                 135                 140
Glu Ala Glu Val Ile Trp Thr Asn Ser Asp His Gln Pro Val Ser Gly
145                 150                 155                 160
Lys Arg Ser Val Thr Thr Ser Arg Thr Glu Gly Met Leu Leu Asn Val
                    165                 170                 175
Thr Ser Ser Leu Arg Val Asn Ala Thr Ala Asn Asp Val Phe Tyr Cys
                180                 185                 190
Thr Phe Trp Arg Ser Gln Pro Gly Gln Asn His Thr Ala Glu Leu Ile
                195                 200                 205
Ile Pro Glu Leu Pro Xaa Xaa Xaa Xaa Xaa Ala Phe Thr Ile Thr
    210                 215                 220
Ala Pro Lys Asp Leu Tyr Val Val Glu Tyr Gly Ser Asn Val Thr Met
225                 230                 235                 240
Glu Cys Arg Phe Pro Val Glu Arg Glu Leu Asp Leu Leu Ala Leu Val
                    245                 250                 255
Val Tyr Trp Glu Lys Glu Asp Glu Gln Val Ile Gln Phe Val Ala Gly
                260                 265                 270
Glu Glu Asp Leu Lys Pro Gln His Ser Asn Phe Arg Gly Arg Ala Ser
                275                 280                 285
Leu Pro Lys Asp Gln Leu Leu Lys Gly Asn Ala Ala Leu Gln Ile Thr
            290                 295                 300
Asp Val Lys Leu Gln Asp Ala Gly Val Tyr Ser Cys Ile Ile Ser Tyr
305                 310                 315                 320
Gly Gly Ala Asp Tyr Lys Arg Ile Thr Leu Lys Val Asn Ala Pro Tyr
                    325                 330                 335
Arg Lys Ile Asn Gln Arg Ile Ser Val Asp Pro Ala Thr Ser Glu His
                340                 345                 350
Glu Leu Ile Cys Gln Ala Glu Gly Tyr Pro Glu Ala Glu Val Ile Trp
                355                 360                 365
Thr Asn Ser Asp His Gln Pro Val Ser Gly Lys Arg Ser Val Thr Thr
            370                 375                 380
Ser Arg Thr Glu Gly Met Leu Leu Asn Val Thr Ser Ser Leu Arg Val
385                 390                 395                 400
Asn Ala Thr Ala Asn Asp Val Phe Tyr Cys Thr Phe Trp Arg Ser Gln
                    405                 410                 415
Pro Gly Gln Asn His Thr Ala Glu Leu Ile Ile Pro Glu Leu Pro Xaa
                420                 425                 430
Xaa Xaa Xaa Xaa Xaa Ala Phe Thr Ile Thr Ala Pro Lys Asp Leu Tyr
            435                 440                 445
Val Val Glu Tyr Gly Ser Asn Val Thr Met Glu Cys Arg Phe Pro Val
            450                 455                 460
Glu Arg Glu Leu Asp Leu Leu Ala Leu Val Val Tyr Trp Glu Lys Glu
465                 470                 475                 480
Asp Glu Gln Val Ile Gln Phe Val Ala Gly Glu Glu Asp Leu Lys Pro
                        485                 490                 495
```

```
Gln His Ser Asn Phe Arg Gly Arg Ala Ser Leu Pro Lys Asp Gln Leu
                500                 505                 510

Leu Lys Gly Asn Ala Ala Leu Gln Ile Thr Asp Val Lys Leu Gln Asp
            515                 520                 525

Ala Gly Val Tyr Ser Cys Ile Ile Ser Tyr Gly Gly Ala Asp Tyr Lys
        530                 535                 540

Arg Ile Thr Leu Lys Val Asn Ala Pro Tyr Arg Lys Ile Asn Gln Arg
545                 550                 555                 560

Ile Ser Val Asp Pro Ala Thr Ser Glu His Glu Leu Ile Cys Gln Ala
                565                 570                 575

Glu Gly Tyr Pro Glu Ala Glu Val Ile Trp Thr Asn Ser Asp His Gln
            580                 585                 590

Pro Val Ser Gly Lys Arg Ser Val Thr Thr Ser Arg Thr Glu Gly Met
        595                 600                 605

Leu Leu Asn Val Thr Ser Ser Leu Arg Val Asn Ala Thr Ala Asn Asp
610                 615                 620

Val Phe Tyr Cys Thr Phe Trp Arg Ser Gln Pro Gly Gln Asn His Thr
625                 630                 635                 640

Ala Glu Leu Ile Ile Pro Glu Leu Pro Xaa Xaa Xaa Xaa Xaa Xaa Ala
                645                 650                 655

Phe Thr Ile Thr Ala Pro Lys Asp Leu Tyr Val Val Glu Tyr Gly Ser
            660                 665                 670

Asn Val Thr Met Glu Cys Arg Phe Pro Val Glu Arg Glu Leu Asp Leu
        675                 680                 685

Leu Ala Leu Val Val Tyr Trp Glu Lys Glu Asp Glu Gln Val Ile Gln
690                 695                 700

Phe Val Ala Gly Glu Glu Asp Leu Lys Pro Gln His Ser Asn Phe Arg
705                 710                 715                 720

Gly Arg Ala Ser Leu Pro Lys Asp Gln Leu Leu Lys Gly Asn Ala Ala
                725                 730                 735

Leu Gln Ile Thr Asp Val Lys Leu Gln Asp Ala Gly Val Tyr Ser Cys
            740                 745                 750

Ile Ile Ser Tyr Gly Gly Ala Asp Tyr Lys Arg Ile Thr Leu Lys Val
        755                 760                 765

Asn Ala Pro Tyr Arg Lys Ile Asn Gln Arg Ile Ser Val Asp Pro Ala
770                 775                 780

Thr Ser Glu His Glu Leu Ile Cys Gln Ala Glu Gly Tyr Pro Glu Ala
785                 790                 795                 800

Glu Val Ile Trp Thr Asn Ser Asp His Gln Pro Val Ser Gly Lys Arg
                805                 810                 815

Ser Val Thr Thr Ser Arg Thr Glu Gly Met Leu Leu Asn Val Thr Ser
            820                 825                 830

Ser Leu Arg Val Asn Ala Thr Ala Asn Asp Val Phe Tyr Cys Thr Phe
        835                 840                 845

Trp Arg Ser Gln Pro Gly Gln Asn His Thr Ala Glu Leu Ile Ile Pro
850                 855                 860

Glu Leu Pro
865

<210> SEQ ID NO 8
<211> LENGTH: 2604
<212> TYPE: DNA
<213> ORGANISM: Artificial sequence
<220> FEATURE:
<221> NAME/KEY: misc_feature
<222> LOCATION: (640)..(657)
```

```
<223> OTHER INFORMATION: n stands for any base
<220> FEATURE:
<221> NAME/KEY: misc_feature
<222> LOCATION: (1294)..(1311)
<223> OTHER INFORMATION: n stands for any base
<220> FEATURE:
<221> NAME/KEY: misc_feature
<222> LOCATION: (1948)..(1965)
<223> OTHER INFORMATION: n stands for any base
<220> FEATURE:
<223> OTHER INFORMATION: Synthetic construct (Tetramer of mouse PD-L1)

<400> SEQUENCE: 8
```

| | | | | | |
|---|---|---|---|---|---|
| atggcgttta | ctatcacggc | tccaaaggac | ttgtacgtgg | tggagtatgg | cagcaacgtc | 60 |
| acgatggagt | gcagattccc | tgtagaacgg | gagctggacc | tgcttgcgtt | agtggtgtac | 120 |
| tgggaaaagg | aagatgagca | agtgattcag | tttgtggcag | gagaggagga | ccttaagcct | 180 |
| cagcacagca | acttcagggg | gagagcctcg | ctgccaaagg | accagctttt | gaagggaaat | 240 |
| gctgcccttc | agatcacaga | cgtcaagctg | caggacgcag | gcgtttacag | ctgcataatc | 300 |
| agctacggtg | gtgcggacta | caagcgaatc | acgctgaaag | tcaatgcccc | ataccgcaaa | 360 |
| atcaaccaga | gaatttccgt | ggatccagcc | acttctgagc | atgaactaat | atgtcaggcc | 420 |
| gagggttatc | cagaagctga | ggtaatctgg | acaaacagtg | accaccaacc | cgtgagtggg | 480 |
| aagagaagtg | tcaccacttc | ccggacagag | gggatgcttc | tcaatgtgac | cagcagtctg | 540 |
| agggtcaacg | ccacagcgaa | tgatgttttc | tactgtacgt | tttggagatc | acagccaggg | 600 |
| caaaaccaca | cagcggagct | gatcatccca | gaactgcctn | nnnnnnnnn | nnnnnnngcg | 660 |
| tttactatca | cggctccaaa | ggacttgtac | gtggtggagt | atggcagcaa | cgtcacgatg | 720 |
| gagtgcagat | ccctgtagaa | cgggagctga | ccctgcttg | cgttagtggt | gtactgggaa | 780 |
| aaggaagatg | agcaagtgat | tcagtttgtg | gcaggagagg | aggaccttaa | gcctcagcac | 840 |
| agcaacttca | gggggagagc | ctcgctgcca | aaggaccagc | ttttgaaggg | aaatgctgcc | 900 |
| cttcagatca | cagacgtcaa | gctgcaggac | gcaggcgttt | acagctgcat | aatcagctac | 960 |
| ggtggtgcgg | actacaagcg | aatcacgctg | aaagtcaatg | ccccataccg | caaaatcaac | 1020 |
| cagagaattt | ccgtggatcc | agccacttct | gagcatgaac | taatatgtca | ggccgagggt | 1080 |
| tatccagaag | ctgaggtaat | ctggacaaac | agtgaccacc | aacccgtgag | tgggaagaga | 1140 |
| agtgtcacca | cttcccggac | agaggggatg | cttctcaatg | tgaccagcag | tctgagggtc | 1200 |
| aacgccacag | cgaatgatgt | tttctactgt | acgttttgga | gatcacagcc | agggcaaaac | 1260 |
| cacacagcgg | agctgatcat | cccagaactg | cctnnnnnnn | nnnnnnnnnn | ngcgtttact | 1320 |
| atcacggctc | caaaggactt | gtacgtggtg | gagtatggca | gcaacgtcac | gatggagtgc | 1380 |
| agattccctg | tagaacggga | gctggacctg | cttgcgttag | tggtgtactg | ggaaaaggaa | 1440 |
| gatgagcaag | tgattcagtt | tgtggcagga | gaggaggacc | ttaagcctca | gcacagcaac | 1500 |
| ttcagggga | gagcctcgct | gccaaaggac | cagcttttga | agggaaatgc | tgcccttcag | 1560 |
| atcacagacg | tcaagctgca | ggacgcaggc | gtttacagct | gcataatcag | ctacggtggt | 1620 |
| gcggactaca | agcgaatcac | gctgaaagtc | aatgccccat | accgcaaaat | caaccagaga | 1680 |
| atttccgtgg | atccagccac | ttctgagcat | gaactaatat | gtcaggccga | gggttatcca | 1740 |
| gaagctgagg | taatctggac | aaacagtgac | caccaacccg | tgagtgggaa | gagaagtgtc | 1800 |
| accacttccc | ggacagaggg | gatgcttctc | aatgtgacca | gcagtctgag | ggtcaacgcc | 1860 |
| acagcgaatg | atgttttcta | ctgtacgttt | tggagatcac | agccagggca | aaaccacaca | 1920 |
| gcggagctga | tcatcccaga | actgcctnnn | nnnnnnnnn | nnnngcgtt | tactatcacg | 1980 |

```
gctccaaagg acttgtacgt ggtggagtat ggcagcaacg tcacgatgga gtgcagattc    2040
cctgtagaac gggagctgga cctgcttgcg ttagtggtgt actgggaaaa ggaagatgag    2100
caagtgattc agtttgtggc aggagaggag gaccttaagc ctcagcacag caacttcagg    2160
gggagagcct cgctgccaaa ggaccagctt ttgaagggaa atgctgccct tcagatcaca    2220
gacgtcaagc tgcaggacgc aggcgtttac agctgcataa tcagctacgg tggtgcggac    2280
tacaagcgaa tcacgctgaa agtcaatgcc ccataccgca aaatcaacca gagaatttcc    2340
gtggatccag ccacttctga gcatgaacta atatgtcagg ccgagggtta tccagaagct    2400
gaggtaatct ggacaaacag tgaccaccaa cccgtgagtg ggaagagaag tgtcaccact    2460
tcccggacag aggggatgct tctcaatgtg accagcagtc tgagggtcaa cgccacagcg    2520
aatgatgttt tctactgtac gttttggaga tcacagccag gcaaaaccacacagcggag    2580 ctgatcatcc cagaactgcc ttaa                                           2604
```

<210> SEQ ID NO 9
<211> LENGTH: 35
<212> TYPE: DNA
<213> ORGANISM: Artificial sequence
<220> FEATURE:
<223> OTHER INFORMATION: Synthetic construct

<400> SEQUENCE: 9

```
cggtagaatt catggcatta gactccccag acagg                               35
```

<210> SEQ ID NO 10
<211> LENGTH: 88
<212> TYPE: DNA
<213> ORGANISM: Artificial sequence
<220> FEATURE:
<223> OTHER INFORMATION: Synthetic construct

<400> SEQUENCE: 10

```
gcgcgtcgac ttaacgatga ttccacacca ccatttctg tgcatccaga atatgatgca    60
gggatcctgt caccctgagc tctgcccg                                        88
```

<210> SEQ ID NO 11
<211> LENGTH: 35
<212> TYPE: DNA
<213> ORGANISM: Artificial sequence
<220> FEATURE:
<223> OTHER INFORMATION: Synthetic construct

<400> SEQUENCE: 11

```
cggtagaatt catggcacta gaggtcccca atggg                               35
```

<210> SEQ ID NO 12
<211> LENGTH: 88
<212> TYPE: DNA
<213> ORGANISM: Artificial sequence
<220> FEATURE:
<223> OTHER INFORMATION: Synthetic construct

<400> SEQUENCE: 12

```
gcgcgtcgac ttaacgatga ttccacacca ccatttctg tgcatccaga atatgatgca    60
gggatcctgt taccacgagc tctgctcc                                        88
```

<210> SEQ ID NO 13
<211> LENGTH: 34
<212> TYPE: DNA
<213> ORGANISM: Artificial sequence
<220> FEATURE:

<223> OTHER INFORMATION: Synthetic construct

<400> SEQUENCE: 13
cggtagaatt catggcattt actgtcacgg ttcc                         34

<210> SEQ ID NO 14
<211> LENGTH: 88
<212> TYPE: DNA
<213> ORGANISM: Artificial sequence
<220> FEATURE:
<223> OTHER INFORMATION: Synthetic construct

<400> SEQUENCE: 14
gcgcgtcgac ttaacgatga ttccacacca ccatttnctg tgcatccaga atatgatgca     60
gggatccagt cctttcattt ggaggatg                                        88

<210> SEQ ID NO 15
<211> LENGTH: 34
<212> TYPE: DNA
<213> ORGANISM: Artificial sequence
<220> FEATURE:
<223> OTHER INFORMATION: Synthetic construct

<400> SEQUENCE: 15
cggtagaatt catggcgttt actatcacgg ctcc                         34

<210> SEQ ID NO 16
<211> LENGTH: 88
<212> TYPE: DNA
<213> ORGANISM: Artificial sequence
<220> FEATURE:
<223> OTHER INFORMATION: Synthetic construct

<400> SEQUENCE: 16
gcgcgtcgac ttaacgatga ttccacacca ccatttnctg tgcatccaga atatgatgca     60
gggatccagg cagttctggg atgatcag                                        88

<210> SEQ ID NO 17
<211> LENGTH: 290
<212> TYPE: PRT
<213> ORGANISM: Homo sapiens

<400> SEQUENCE: 17

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

```
Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 18
<211> LENGTH: 290
<212> TYPE: PRT
<213> ORGANISM: Mus musculus

<400> SEQUENCE: 18

Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
                20                  25                  30

Gly Ser Asn Val Thr Met Glu Cys Arg Phe Pro Val Glu Arg Glu Leu
            35                  40                  45

Asp Leu Leu Ala Leu Val Val Tyr Trp Glu Lys Glu Asp Glu Gln Val
        50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
130                 135                 140

Pro Ala Thr Ser Glu His Glu Leu Ile Cys Gln Ala Glu Gly Tyr Pro
                150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220
```

```
Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
            275                 280                 285

Glu Thr
    290
```

The invention claimed is:

1. A multimer comprising 2 to 10 extracellular domains of Programmed Cell Death-Ligand 1 (PD-L1), wherein the extracellular domains of PD-L1 are serially-concatenated directly or with peptide linkers, and wherein said PD-L1 is human PD-L1 or mouse PD-L1, wherein the human PD-L1 has the amino acid sequence SEQ ID NO: 17, and wherein the mouse PD-L1 has the amino acid sequence of SEQ ID NO: 18.

2. The multimer according to claim 1, wherein each of the extracellular domains of PD-L1 comprises a region selected from (a) and (b):

(a) residues 1-238 or residues 18-230 of human PD-L1; and (b) residues 1-237 or residues 18-229 of mouse PD-L1.

3. The multimer according to claim 2, wherein 1 to 3 amino acid(s) in each of the extracellular domains of PD-L1 is/are substituted by other amino acid(s).

4. The multimer according to claim 1, wherein the multimer is a tetramer.

5. The multimer according to claim 1, wherein each of the extracellular domains of PD-L1 is serially-concatenated with peptide linkers.

6. The multimer according to claim 1, wherein each peptide linker comprises 2 to 15 amino acids.

7. The multimer according to 2to 10 extracellular domains of Programmed Cell Death-Ligand (PD-L1) wherein the extracellular of PD-L1 are bound to a carrier via a non-peptide linker, and wherein said PD-L1 or mouse PD-L1, wherein the human PD-L1 has the amino acid sequence of SEQ ID NO: 17, and wherein the mouse PD-L1 has the amino acid sequence of SEQ ID NO: 18.

8. The multimer according to claim 7, wherein the carrier is an avidin streptavidin or a derivative thereof and the non-peptide linker is a biotin.

9. The multimer according to claim 6, comprising the amino acid sequence of SEQ ID NO: 5 or 7.

10. A pharmaceutical composition comprising the multimer according to claim 1 as an active ingredient.

11. A pharmaceutical composition comprising the multimer according to claim 1 and at least one ingredient selected from the group consisting of chemotherapy drugs, cancer treatment adjuvants, immunomodulators, cancer antigens, antiviral agents, antibiotic preparations, antimicrobials, fungal treatments and vaccines.

12. A Programmed Cell Death-1 detection reagent comprising the multimer according to claim 1.

13. A method of treatment of cancers, cancer metastasis, immune deficiency syndrome or infectious diseases, comprising administering an effective amount of the multimer according to claim 1 to a patient in need thereof.

* * * * *